United States Patent
Dickhans et al.

(10) Patent No.: US 11,197,715 B2
(45) Date of Patent: Dec. 14, 2021

(54) ABLATION CABLE ASSEMBLIES AND A METHOD OF MANUFACTURING THE SAME

(71) Applicant: COVIDIEN LP, Mansfield, MA (US)

(72) Inventors: William J. Dickhans, Longmont, CO (US); John J. Halbur, Woodridge, IL (US); Joseph D. Brannan, Lyons, CO (US)

(73) Assignee: COVIDIEN LP, Mansfield, MA (US)

( * ) Notice: Subject to any disclaimer, the term of this patent is extended or adjusted under 35 U.S.C. 154(b) by 567 days.

(21) Appl. No.: 15/225,945

(22) Filed: Aug. 2, 2016

(65) Prior Publication Data

US 2018/0036070 A1  Feb. 8, 2018

(51) Int. Cl.
| | | |
|---|---|---|
| *A61B 18/18* | (2006.01) | |
| *A61B 18/14* | (2006.01) | |
| *A61B 18/00* | (2006.01) | |

(52) U.S. Cl.
CPC ............. *A61B 18/1492* (2013.01); *A61B 2018/00577* (2013.01); *A61B 2018/144* (2013.01); *A61B 2018/1465* (2013.01)

(58) Field of Classification Search
CPC ............ A61B 18/1815; A61B 18/1492; A61B 2018/00077; A61B 2018/00577; A61B 2018/00982; A61B 2018/1838; A61B 2018/1892; A61B 2018/144; A61B 2018/1465; A61B 18/1477; A61B 2018/183; A61B 2562/222; A61B 2018/1884; A61B 2018/1815; A61B 2018/1807; A61B 2018/1861; A61B 2018/1869; A61B 2018/1876;
(Continued)

(56) References Cited

U.S. PATENT DOCUMENTS

| | | | | |
|---|---|---|---|---|
| 3,375,485 A | * | 3/1968 | Donohue | ................ H01R 9/05 439/581 |
| D223,367 S | | 4/1972 | Kountz | |

(Continued)

FOREIGN PATENT DOCUMENTS

| | | |
|---|---|---|
| CN | 1103807 A | 6/1995 |
| DE | 179607 C | 3/1905 |

(Continued)

OTHER PUBLICATIONS

U.S. Appl. No. 14/242,019, filed Apr. 1, 2014; inventor: Brannan.
(Continued)

*Primary Examiner* — Thomas A Giuliani
*Assistant Examiner* — Christine A Dedoulis
(74) *Attorney, Agent, or Firm* — Carter, DeLuca & Farrell LLP

(57) ABSTRACT

A cable assembly includes a rigid portion, a flexible central portion, and a radiating portion. The rigid portion is configured to couple to a source of electrosurgical energy and to prevent fluid ingress towards the source of electrosurgical energy. The flexible central portion extends from the rigid portion and includes an inner conductor, a dielectric disposed about the inner conductor, and a conductive braid disposed about the dielectric. The radiating portion extends from the central portion and is configured to deliver electrosurgical energy to tissue.

20 Claims, 14 Drawing Sheets

(58) Field of Classification Search
CPC ............. H01B 13/2626; H01B 11/06; H01B 11/1033; H01R 4/70; H01R 4/72
See application file for complete search history.

(56) References Cited

U.S. PATENT DOCUMENTS

| | | | |
|---|---|---|---|
| 4,014,343 A | 3/1977 | Esty | |
| D263,020 S | 2/1982 | Rau, III | |
| D266,842 S | 11/1982 | Villers et al. | |
| D278,306 S | 4/1985 | McIntosh | |
| D295,893 S | 5/1988 | Sharkany et al. | |
| D295,894 S | 5/1988 | Sharkany et al. | |
| 4,822,952 A * | 4/1989 | Katz | H02G 15/064 156/49 |
| 4,896,671 A | 1/1990 | Cunningham et al. | |
| 5,301,687 A | 4/1994 | Wong et al. | |
| 5,364,392 A | 11/1994 | Warner et al. | |
| 5,370,644 A | 12/1994 | Langberg | |
| D354,218 S | 1/1995 | Van de Peer | |
| 5,545,137 A | 8/1996 | Rudie et al. | |
| 5,556,377 A | 9/1996 | Rosen et al. | |
| 5,603,697 A | 2/1997 | Grundy et al. | |
| 5,624,392 A | 4/1997 | Saab | |
| 5,685,839 A | 11/1997 | Edwards et al. | |
| 5,693,082 A | 12/1997 | Warner et al. | |
| 5,741,249 A | 4/1998 | Moss et al. | |
| 5,871,481 A | 2/1999 | Kannenberg et al. | |
| 5,961,871 A | 10/1999 | Bible et al. | |
| 5,980,505 A | 11/1999 | Wilson | |
| 5,993,447 A | 11/1999 | Blewett et al. | |
| 5,995,875 A | 11/1999 | Blewett et al. | |
| 6,014,581 A | 1/2000 | Whayne et al. | |
| D424,693 S | 5/2000 | Pruter | |
| D424,694 S | 5/2000 | Tetzlaff et al. | |
| D425,201 S | 5/2000 | Tetzlaff et al. | |
| 6,061,551 A | 5/2000 | Sorrells et al. | |
| 6,097,985 A * | 8/2000 | Kasevich | A61B 18/18 607/100 |
| 6,106,524 A | 8/2000 | Eggers et al. | |
| 6,117,101 A | 9/2000 | Diederich et al. | |
| 6,139,527 A | 10/2000 | Laufer et al. | |
| 6,186,978 B1 | 2/2001 | Samson et al. | |
| 6,210,367 B1 | 4/2001 | Carr | |
| 6,235,024 B1 | 5/2001 | Tu | |
| 6,277,113 B1 | 8/2001 | Berube | |
| D449,886 S | 10/2001 | Tetzlaff et al. | |
| 6,355,016 B1 | 3/2002 | Bagaoisan et al. | |
| D457,958 S | 5/2002 | Dycus et al. | |
| D457,959 S | 5/2002 | Tetzlaff et al. | |
| 6,383,183 B1 | 5/2002 | Sekino et al. | |
| 6,398,781 B1 | 6/2002 | Goble et al. | |
| 6,485,486 B1 | 11/2002 | Trembly et al. | |
| 6,496,737 B2 | 12/2002 | Rudie et al. | |
| 6,496,738 B2 | 12/2002 | Carr | |
| 6,511,478 B1 | 1/2003 | Burnside et al. | |
| 6,514,249 B1 | 2/2003 | Maguire et al. | |
| 6,547,788 B1 | 4/2003 | Maguire et al. | |
| 6,575,969 B1 | 6/2003 | Rittman, III et al. | |
| 6,599,288 B2 | 7/2003 | Maguire et al. | |
| 6,629,974 B2 | 10/2003 | Penny et al. | |
| 6,635,055 B1 | 10/2003 | Cronin | |
| 6,652,515 B1 | 11/2003 | Maguire et al. | |
| 6,676,657 B2 | 1/2004 | Wood | |
| D487,039 S | 2/2004 | Webster et al. | |
| 6,706,040 B2 | 3/2004 | Mahon et al. | |
| 6,723,091 B2 | 4/2004 | Goble et al. | |
| 6,740,108 B1 | 5/2004 | Just et al. | |
| 6,770,070 B1 | 8/2004 | Balbierz | |
| 6,780,183 B2 | 8/2004 | Jimenez, Jr. et al. | |
| D496,997 S | 10/2004 | Dycus et al. | |
| D499,181 S | 11/2004 | Dycus et al. | |
| 6,847,848 B2 | 1/2005 | Sterzer et al. | |
| 6,869,431 B2 | 3/2005 | Maguire et al. | |
| 6,878,147 B2 * | 4/2005 | Prakash | A61B 18/18 606/33 |
| 6,893,436 B2 | 5/2005 | Woodard et al. | |
| 6,932,776 B2 | 8/2005 | Carr | |
| 6,997,925 B2 | 2/2006 | Maguire et al. | |
| 7,004,938 B2 | 2/2006 | Ormsby et al. | |
| 7,047,068 B2 | 5/2006 | Haissaguerre | |
| 7,049,068 B2 | 5/2006 | Thorp et al. | |
| D525,361 S | 7/2006 | Hushka | |
| 7,089,063 B2 | 8/2006 | Lesh et al. | |
| 7,113,832 B2 | 9/2006 | Longo | |
| D531,311 S | 10/2006 | Guerra et al. | |
| D533,942 S | 12/2006 | Kerr et al. | |
| D535,027 S | 1/2007 | James et al. | |
| 7,197,356 B2 | 3/2007 | Carr | |
| D541,418 S | 4/2007 | Schechter et al. | |
| 7,200,445 B1 | 4/2007 | Dalbec et al. | |
| D541,938 S | 5/2007 | Kerr et al. | |
| 7,261,001 B2 | 8/2007 | Heijnsdijk et al. | |
| 7,263,398 B2 | 8/2007 | Carr | |
| 7,275,547 B2 | 10/2007 | Willis | |
| 7,285,116 B2 | 10/2007 | de la Rama et al. | |
| 7,294,125 B2 | 11/2007 | Phalen et al. | |
| 7,300,436 B2 | 11/2007 | Penny et al. | |
| 7,303,558 B2 | 12/2007 | Swanson | |
| D564,662 S | 3/2008 | Moses et al. | |
| 7,402,168 B2 | 7/2008 | Sanderson et al. | |
| D574,323 S | 8/2008 | Waaler | |
| 7,410,486 B2 | 8/2008 | Fuimaono et al. | |
| D576,932 S | 9/2008 | Strehler | |
| 7,438,712 B2 | 10/2008 | Chouinard | |
| 7,460,898 B2 | 12/2008 | Brister et al. | |
| 7,467,015 B2 | 12/2008 | van der Weide | |
| 7,507,229 B2 | 3/2009 | Hewitt et al. | |
| D594,736 S | 6/2009 | Esjunin | |
| D594,737 S | 6/2009 | Kelly et al. | |
| 7,608,056 B2 | 10/2009 | Kennedy, II | |
| 7,611,508 B2 | 11/2009 | Yang et al. | |
| D606,203 S | 12/2009 | Husheer et al. | |
| D613,412 S | 4/2010 | DeCarlo | |
| 7,697,972 B2 | 4/2010 | Verard et al. | |
| 7,706,894 B2 | 4/2010 | Stewart et al. | |
| 7,713,259 B2 | 5/2010 | Gosiengfiao et al. | |
| 7,722,604 B2 | 5/2010 | Brown, III et al. | |
| 7,734,330 B2 | 6/2010 | Carr | |
| 7,769,469 B2 | 8/2010 | Carr et al. | |
| 7,824,392 B2 | 11/2010 | Zhou | |
| 7,826,904 B2 | 11/2010 | Appling et al. | |
| 7,833,218 B2 | 11/2010 | Lunn et al. | |
| 7,863,984 B1 | 1/2011 | Behnke | |
| D634,010 S | 3/2011 | DeCarlo | |
| 7,921,855 B2 | 4/2011 | Danek et al. | |
| 7,933,660 B2 | 4/2011 | Carr | |
| 7,993,351 B2 | 8/2011 | Worley et al. | |
| 8,021,351 B2 | 9/2011 | Boldenow et al. | |
| 8,075,532 B2 | 12/2011 | Kassab et al. | |
| 8,182,466 B2 | 5/2012 | Stehr et al. | |
| 8,206,373 B2 | 6/2012 | Zhou | |
| 8,206,380 B2 | 6/2012 | Lenihan et al. | |
| 8,226,566 B2 | 7/2012 | Nita | |
| 8,277,438 B2 | 10/2012 | Griffin et al. | |
| 8,289,551 B2 | 10/2012 | Wu | |
| 8,292,881 B2 | 10/2012 | Brannan et al. | |
| 8,328,799 B2 | 12/2012 | Brannan | |
| 8,328,800 B2 | 12/2012 | Brannan | |
| 8,328,801 B2 | 12/2012 | Brannan | |
| 8,340,740 B2 | 12/2012 | Holzer et al. | |
| 8,343,145 B2 | 1/2013 | Brannan | |
| 8,353,903 B2 | 1/2013 | Podhajsky | |
| 8,394,092 B2 | 3/2013 | Brannan | |
| 8,412,306 B2 | 4/2013 | Kurpad et al. | |
| D681,810 S | 5/2013 | DeCarlo | |
| 8,459,525 B2 | 6/2013 | Yates et al. | |
| 8,491,579 B2 | 7/2013 | Rossetto | |
| 8,515,554 B2 | 8/2013 | Carr | |
| 8,655,454 B2 | 2/2014 | Prakash et al. | |
| 8,672,932 B2 | 3/2014 | van der Weide et al. | |
| 8,795,268 B2 | 8/2014 | Willyard | |
| 9,023,025 B2 | 5/2015 | Behnke, II et al. | |
| 9,247,992 B2 | 2/2016 | Ladtkow et al. | |
| 2002/0022836 A1 | 2/2002 | Goble et al. | |

(56) References Cited

U.S. PATENT DOCUMENTS

| | | |
|---|---|---|
| 2002/0156471 A1 | 10/2002 | Stern et al. |
| 2003/0191451 A1 | 10/2003 | Gilmartin |
| 2003/0195499 A1* | 10/2003 | Prakash .............. A61B 18/14 606/33 |
| 2005/0015081 A1 | 1/2005 | Turovskiy et al. |
| 2005/0215942 A1 | 9/2005 | Abrahamson et al. |
| 2006/0009833 A1 | 1/2006 | Chobotov et al. |
| 2006/0089637 A1 | 4/2006 | Werneth et al. |
| 2006/0155270 A1 | 7/2006 | Hancock et al. |
| 2006/0167416 A1 | 7/2006 | Mathis et al. |
| 2006/0241564 A1 | 10/2006 | Corcoran et al. |
| 2006/0253102 A1 | 11/2006 | Nance et al. |
| 2006/0282069 A1 | 12/2006 | Prakash et al. |
| 2007/0088319 A1 | 4/2007 | Martone |
| 2007/0287912 A1 | 12/2007 | Khuri-Yakub et al. |
| 2008/0091169 A1 | 4/2008 | Heideman et al. |
| 2008/0147056 A1 | 6/2008 | van der Weide et al. |
| 2008/0208039 A1 | 8/2008 | Kurpad et al. |
| 2008/0228167 A1 | 9/2008 | Mittermeyer et al. |
| 2008/0249523 A1 | 10/2008 | McPherson et al. |
| 2008/0255507 A1 | 10/2008 | Mushtaha |
| 2008/0294162 A1* | 11/2008 | Rossetto .............. A61B 18/14 606/50 |
| 2009/0005766 A1 | 1/2009 | Brannan |
| 2009/0076409 A1 | 3/2009 | Wu et al. |
| 2009/0187180 A1 | 7/2009 | Brannan |
| 2009/0222002 A1 | 9/2009 | Bonn et al. |
| 2009/0234220 A1 | 9/2009 | Maschke |
| 2010/0036369 A1 | 2/2010 | Hancock |
| 2010/0049177 A1 | 2/2010 | Boone, III et al. |
| 2010/0079215 A1 | 4/2010 | Brannan et al. |
| 2010/0082022 A1 | 4/2010 | Haley et al. |
| 2010/0082023 A1 | 4/2010 | Brannan et al. |
| 2010/0082024 A1 | 4/2010 | Brannan et al. |
| 2010/0082025 A1 | 4/2010 | Brannan et al. |
| 2010/0082083 A1 | 4/2010 | Brannan et al. |
| 2010/0082084 A1 | 4/2010 | Brannan et al. |
| 2010/0087808 A1 | 4/2010 | Paulus |
| 2010/0094271 A1 | 4/2010 | Ward et al. |
| 2010/0097284 A1* | 4/2010 | Brannan ............ A61B 18/1815 343/793 |
| 2010/0179455 A1 | 7/2010 | Nebrigic et al. |
| 2010/0262134 A1 | 10/2010 | Jensen et al. |
| 2010/0268196 A1 | 10/2010 | Hastings et al. |
| 2010/0268220 A1 | 10/2010 | Johnson et al. |
| 2010/0286681 A1 | 11/2010 | Podhajsky |
| 2010/0286682 A1 | 11/2010 | Podhajsky |
| 2010/0286683 A1 | 11/2010 | Podhajsky |
| 2010/0305559 A1 | 12/2010 | Brannan et al. |
| 2010/0312234 A1 | 12/2010 | Mahvi et al. |
| 2011/0004205 A1 | 1/2011 | Chu et al. |
| 2011/0066144 A1 | 3/2011 | Bonn et al. |
| 2011/0077639 A1 | 3/2011 | Brannan et al. |
| 2011/0115562 A1 | 5/2011 | Gilbert |
| 2011/0130750 A1 | 6/2011 | Ormsby et al. |
| 2011/0166518 A1 | 7/2011 | Nguyen et al. |
| 2011/0166519 A1 | 7/2011 | Nguyen et al. |
| 2011/0196362 A1 | 8/2011 | Rossetto |
| 2011/0276113 A1 | 11/2011 | Cybulski |
| 2011/0282336 A1 | 11/2011 | Brannan et al. |
| 2011/0301587 A1 | 12/2011 | Deem et al. |
| 2011/0319880 A1 | 12/2011 | Prakash et al. |
| 2012/0004652 A1 | 1/2012 | Moua et al. |
| 2012/0065481 A1 | 3/2012 | Hunter et al. |
| 2012/0071822 A1 | 3/2012 | Romo et al. |
| 2012/0078175 A1 | 3/2012 | Vreeman |
| 2012/0078230 A1 | 3/2012 | Lowe et al. |
| 2012/0259326 A1 | 10/2012 | Brannan et al. |
| 2012/0277730 A1 | 11/2012 | Salahieh et al. |
| 2013/0137977 A1 | 5/2013 | Eder |
| 2013/0197481 A1 | 8/2013 | Guo et al. |
| 2013/0197482 A1 | 8/2013 | Akitomo |
| 2013/0237980 A1 | 9/2013 | Brannan |
| 2013/0241769 A1 | 9/2013 | Brannan et al. |
| 2013/0245624 A1 | 9/2013 | Bahney |
| 2013/0253500 A1 | 9/2013 | Lee et al. |
| 2013/0261617 A1 | 10/2013 | Podhajsky |
| 2013/0261620 A1 | 10/2013 | Brannan et al. |
| 2013/0267946 A1 | 10/2013 | Brannan et al. |
| 2013/0289560 A1 | 10/2013 | DeCarlo et al. |
| 2013/0296841 A1 | 11/2013 | Brannan |
| 2013/0304057 A1 | 11/2013 | Rossetto |
| 2013/0317407 A1 | 11/2013 | Reid, Jr. et al. |
| 2013/0317495 A1 | 11/2013 | Brannan |
| 2013/0317499 A1 | 11/2013 | Brannan et al. |
| 2013/0324910 A1 | 12/2013 | Ohri et al. |
| 2013/0324911 A1 | 12/2013 | Ohri et al. |
| 2013/0338661 A1 | 12/2013 | Behnke, II |
| 2013/0345541 A1 | 12/2013 | Nau, Jr. |
| 2013/0345551 A1 | 12/2013 | Arts et al. |
| 2013/0345552 A1 | 12/2013 | Arts et al. |
| 2013/0345553 A1 | 12/2013 | Arts et al. |
| 2013/0345699 A1 | 12/2013 | Brannan et al. |
| 2014/0000098 A1 | 1/2014 | Dunning et al. |
| 2014/0005655 A1 | 1/2014 | Brannan |
| 2014/0005657 A1 | 1/2014 | Brannan et al. |
| 2014/0018668 A1 | 1/2014 | Zheng et al. |
| 2014/0018677 A1 | 1/2014 | Sharonov |
| 2014/0018793 A1 | 1/2014 | Sharonov |
| 2014/0046174 A1* | 2/2014 | Ladtkow .............. A61B 1/018 600/424 |
| 2014/0046175 A1 | 2/2014 | Ladtkow et al. |
| 2014/0094789 A1 | 4/2014 | Brannan |
| 2014/0094792 A1 | 4/2014 | Sharonov |
| 2014/0094794 A1 | 4/2014 | Orszulak |
| 2014/0094797 A1 | 4/2014 | Brannan |
| 2014/0240830 A1 | 8/2014 | Chae et al. |
| 2014/0290830 A1* | 10/2014 | Brannan .............. A61B 18/1815 156/86 |
| 2015/0022342 A1 | 1/2015 | Will et al. |
| 2015/0065964 A1 | 3/2015 | Ohri et al. |
| 2015/0148793 A1 | 5/2015 | Brannan |

FOREIGN PATENT DOCUMENTS

| | | |
|---|---|---|
| DE | 390937 C | 3/1924 |
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 8712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 4206433 A1 | 9/1993 |
| DE | 04303882 C2 | 2/1995 |
| DE | 4339049 A1 | 5/1995 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |

(56) References Cited

FOREIGN PATENT DOCUMENTS

| | | |
|---|---|---|
| DE | 19848540 A1 | 5/2000 |
| DE | 10217281 A1 | 10/2003 |
| DE | 10224154 A1 | 12/2003 |
| DE | 10310765 A1 | 9/2004 |
| DE | 10328514 B3 | 3/2005 |
| DE | 102004022206 A1 | 12/2005 |
| DE | 202005015147 U1 | 2/2006 |
| DE | 102009015699 A1 | 5/2010 |
| EP | 0 246 350 A1 | 11/1987 |
| EP | 267403 A2 | 5/1988 |
| EP | 296777 A2 | 12/1988 |
| EP | 310431 A2 | 4/1989 |
| EP | 325456 A2 | 7/1989 |
| EP | 336742 A2 | 10/1989 |
| EP | 390937 A1 | 10/1990 |
| EP | 0 521 264 A2 | 1/1993 |
| EP | 0 556 705 A1 | 8/1993 |
| EP | 0 558 429 A1 | 9/1993 |
| EP | 608609 A2 | 8/1994 |
| EP | 0 648 515 A1 | 4/1995 |
| EP | 0 836 868 A2 | 4/1998 |
| EP | 880220 A2 | 11/1998 |
| EP | 0 882 955 A1 | 12/1998 |
| EP | 1034747 A1 | 9/2000 |
| EP | 1034748 A1 | 9/2000 |
| EP | 1051948 A2 | 11/2000 |
| EP | 1055400 A1 | 11/2000 |
| EP | 1159926 A3 | 3/2003 |
| EP | 1366724 A1 | 12/2003 |
| EP | 1776929 A1 | 4/2007 |
| EP | 2147651 A1 | 1/2010 |
| EP | 2322113 A1 | 5/2011 |
| EP | 2345454 A1 | 7/2011 |
| FR | 179 607 | 11/1906 |
| FR | 1 275 415 A | 11/1961 |
| FR | 1 347 865 A | 1/1964 |
| FR | 2 235 669 A1 | 1/1975 |
| FR | 2 276 027 A1 | 1/1976 |
| FR | 2 313 708 A1 | 12/1976 |
| FR | 2364461 A1 | 4/1978 |
| FR | 2 502 935 A1 | 10/1982 |
| FR | 2 517 953 A1 | 6/1983 |
| FR | 2 573 301 A1 | 5/1986 |
| FR | 2 862 813 A1 | 5/2005 |
| FR | 2 864 439 A1 | 7/2005 |
| JP | 56-161636 | 12/1981 |
| JP | 59-58933 | 4/1984 |
| JP | 5-5106 | 1/1993 |
| JP | 5-08933 | 2/1993 |
| JP | 05-40112 | 2/1993 |
| JP | 06343644 A | 12/1994 |
| JP | 07265328 A | 10/1995 |
| JP | 08056955 | 3/1996 |
| JP | 08252263 A | 10/1996 |
| JP | 09000492 A | 1/1997 |
| JP | 09010223 | 1/1997 |
| JP | 9117456 | 5/1997 |
| JP | 11244298 A | 9/1999 |
| JP | 2000342599 A | 12/2000 |
| JP | 2000350732 A | 12/2000 |
| JP | 2001003776 A | 1/2001 |
| JP | 2001008944 A | 1/2001 |
| JP | 2001029356 A | 2/2001 |
| JP | 2001037775 A | 2/2001 |
| JP | 2001128990 A | 5/2001 |
| JP | 2001231870 A | 8/2001 |
| JP | 2002253569 A | 9/2002 |
| JP | 2008142467 A | 6/2008 |
| KR | 20070093068 A | 9/2007 |
| KR | 20100014406 A | 2/2010 |
| KR | 20120055063 A | 5/2012 |
| SU | 166452 | 1/1965 |
| SU | 401367 A1 | 10/1973 |
| SU | 727201 A2 | 4/1980 |
| WO | 9416632 A1 | 8/1994 |
| WO | 9724074 A1 | 7/1997 |
| WO | 00/36985 A2 | 6/2000 |
| WO | 0057811 A1 | 10/2000 |
| WO | 0100114 A1 | 1/2001 |
| WO | 0211634 A1 | 2/2002 |
| WO | 0245589 A2 | 6/2002 |
| WO | 0245790 A2 | 6/2002 |
| WO | 03090635 A1 | 11/2003 |
| WO | 2006050888 A1 | 5/2006 |
| WO | 2008053532 A1 | 5/2008 |
| WO | 2008068485 A2 | 6/2008 |
| WO | 2010/035831 A1 | 4/2010 |
| WO | 2010129348 A1 | 11/2010 |

OTHER PUBLICATIONS

U.S. Appl. No. 14/242,048, filed Apr. 1, 2014; inventor: Prakash.
U.S. Appl. No. 14/281,264, filed May 19, 2014; inventor: Prakash.
U.S. Appl. No. 14/281,344, filed May 19, 2014; inventor: Shiu.
U.S. Appl. No. 14/300,824, filed Jun. 10, 2014; inventor: Behnke.
U.S. Appl. No. 14/300,871, filed Jun. 10, 2014; inventor: Bonn.
U.S. Appl. No. 14/306,865, filed Jun. 17, 2014; inventor: Brannan.
U.S. Appl. No. 15/225,890, filed Aug. 2, 2016; inventor Dickhans.
U.S. Appl. No. 15/226,019, filed Aug. 2, 2016; inventor Dickhans.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure.TM. Device in the Hemostasis of Small, Medium, and Large-Sized Arteries" Carolinas Laparoscopic and Advanced Surgery Program, Carolinas Medical Center,Charlotte, NC 2003.

(56) References Cited

OTHER PUBLICATIONS

Carus et al., "Initial Experience With the LigaSure.TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSureTM" Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw-Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15: (1984), pp. 945-950.
Crawford et al., "Use of the LigaSure.TM. Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales Product Literature 2000.
Esterline, "Light Key Projection Keyboard" Advanced Input Systems, located at: <http://www.advanced-input.com/ightkey> 2002.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSureTM Vessel Sealing System: A Case Report" Innovations That Work, Feb. 2002.
Humphries Jr. et al., "Finite Element Codes To Model Electrical Heating And Non-Linear Thermal Transport In Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSureTM Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSureTM Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol. BME-31, No. 1, Jan. 1984, pp. 28-37.
Johnson, "Use of the LigaSureTM Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, " LigaSureTM System Used in Laparoscopic 1st and 2nd Stage Orchiopexy" Innovations That Work, Nov. 2002.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSureTM Vessel Sealing System, the Seal of Confidence in General, Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-lridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSureTM Vessel Sealing System and LigaSureTM Atlas 20 cm Open Instrument" Innovations That Work, Jun. 2003.
Muller et al., "Extended Left Hemicolectomy Using the LigaSureTM Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences•Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSureTM versus open haemorrhoidectomy" British Journal of Surgery 2002,89,154-157 "Innovations in Electrosurgery" Sales/Product Literature; Dec. 31, 2000.

(56) References Cited

OTHER PUBLICATIONS

Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSureTM Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Longterm Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Stagegaard, N., Petersen H.H., Chen X., Svendsen J.H., "Indication of the Radiofrequency Induced Lesion Size by Pre-ablation Measurements" Europace (2005) 7, 525-534.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817-825.
Urologix, Inc.—Medical Professionals: TargisTM Technology (Date Unknown). "Overcoming the Challenge" located at <http://www.urologix.com!medicaUtechnology.html > Nov. 18, 1999; 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation-'COA-COMP'" Neurosurgical Review 7:2-3 (1984) pp. 187-190.
W. Scott Helton, "LigaSureTM Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
U.S. Appl. No. 08/136,098, filed Oct. 14, 1993; Roger A. Stern.
U.S. Appl. No. 08/483,742, filed Jun. 7, 1995; Roger A. Stern.
U.S. Appl. No. 14/011,414, filed Aug. 27, 2013; inventor: Ohri.
U.S. Appl. No. 14/011,438, filed Aug. 27, 2013; inventor: Ohri.

* cited by examiner

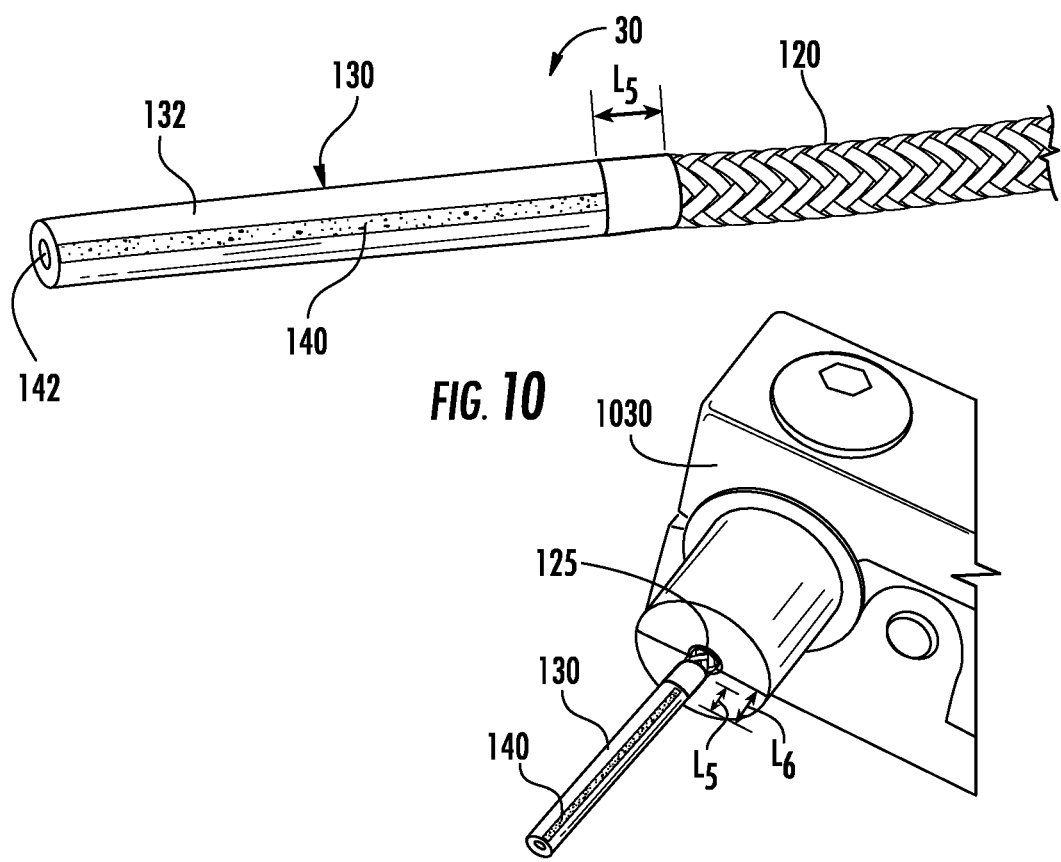
FIG. 10
FIG. 11
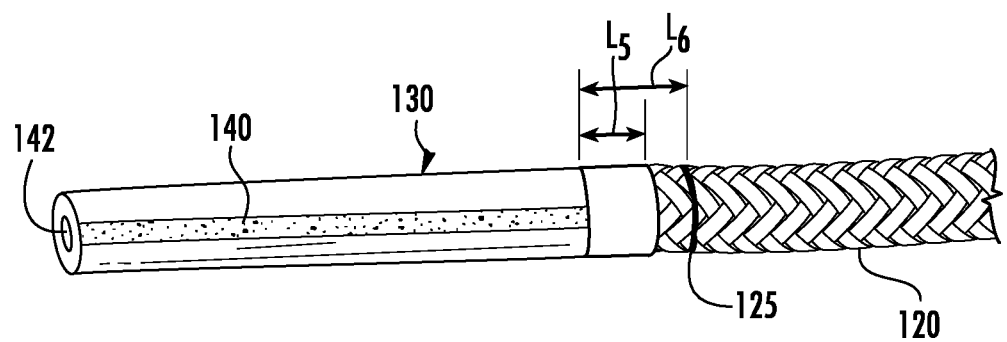
FIG. 12
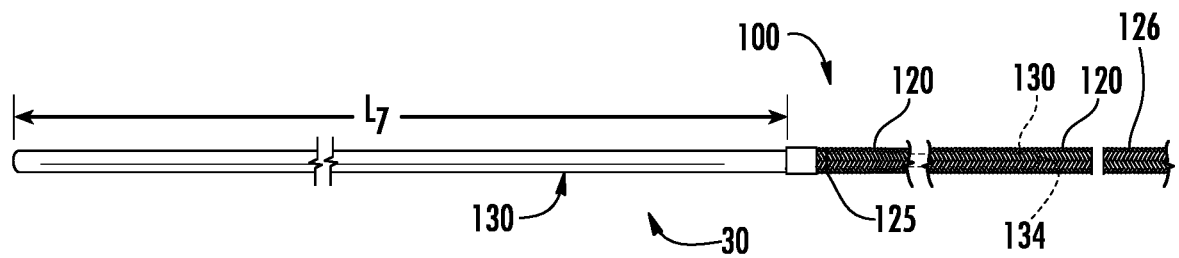
FIG. 13

ABLATION CABLE ASSEMBLIES AND A METHOD OF MANUFACTURING THE SAME

BACKGROUND

1. Technical Field

The present disclosure relates to surgical instruments and, more specifically, to ablation cable assemblies.

2. Discussion of Related Art

Electromagnetic fields can be used to heat and destroy tumor cells. Treatment may involve inserting ablation probes into tissues where cancerous tumors have been identified. Once the ablation probes are properly positioned, the ablation probes induce electromagnetic fields within the tissue surrounding the ablation probes.

In the treatment of diseases such as cancer, certain types of tumor cells have been found to denature at elevated temperatures that are slightly lower than temperatures normally injurious to healthy cells. Known treatment methods, such as hyperthermia therapy, heat diseased cells to temperatures above 41° C. while maintaining adjacent healthy cells below the temperature at which irreversible cell destruction occurs. These methods involve applying electromagnetic fields to heat or ablate tissue.

Devices utilizing electromagnetic fields have been developed for a variety of uses and applications. Typically, apparatuses for use in ablation procedures include a power generation source, e.g., a microwave generator that functions as an energy source and a surgical instrument (e.g., microwave ablation probe having an antenna assembly) for directing energy to the target tissue. The generator and surgical instrument are typically operatively coupled by a cable assembly having a plurality of conductors for transmitting energy from the generator to the instrument, and for communicating control, feedback, and identification signals between the instrument and the generator.

As electromagnetic fields can be induced at a distance by microwave probes, microwave ablation has the potential to create large active zones whose shapes can be determined and held constant by design. Furthermore, the shape and size can be determined through design to fit a specific medical application. By utilizing a predetermined active zone to create a predictable ablation zone, and not relying upon the indeterminate passive ablation zone, microwave ablation can provide a level of predictability and procedural relevance not possible with other ablative techniques.

The shape of the active zone about an antenna is determined by the frequency of operation, the geometry of the antenna, the materials of the antenna, and the medium surrounding the antenna. Operating an antenna in a medium of dynamically changing electrical properties, such as heating tissue, results in a changing shape of the electromagnetic field, and therefore a changing shape of the active zone. To maintain the shape of the active zone about a microwave antenna, the degree of influence on the electromagnetic field of the surrounding medium's electrical properties are reduced.

The size of the active zone about an antenna is determined by the amount of energy which can be delivered to the antenna. With more energy delivered to the antenna, larger active zones can be generated. To maximize the energy delivered to the antenna, the size of an inner conductor of the cable assembly and a dielectric of the cable assembly about the inner conductor should be maximized and the size of an outer conductor of the cable assembly should be minimized.

SUMMARY

This disclosure relates generally to an ablation cable assembly that includes a water tight semi-rigid proximal portion and a flexible distal portion. The flexible distal portion includes an exposed outer conductor that can be in contact fluids such as dielectric fluids, cooling fluids, or bodily fluids. As detailed below, the thickness of the outer conductor is minimized to allow a larger thickness of a dielectric and an inner conductor for a given diameter of the cable assembly.

In an aspect of the present disclosure, a cable assembly includes a rigid portion, a flexible central portion, and an radiating portion. The rigid portion is configured to couple to a source of electrosurgical energy and to prevent fluid ingress. The flexible central portion extends from the rigid portion and includes an inner conductor, a dielectric disposed about the inner conductor, and a conductive braid disposed about the dielectric. The radiating portion extends from the central portion and is configured to deliver electrosurgical energy to tissue.

In aspects, the conductive braid is pregnable by fluid. The rigid portion and the central portion may be configured to deliver at least 150 watts of continuous electrosurgical energy to the radiating portion. The entire cable assembly may have a diameter in a range of less than about 0.01 inches to about 0.5 inches, 0.02 inches to about 0.4 inches, 0.03 inches to about 0.3 inches, 0.04 inches to about 0.2 inches, 0.05 inches to about 0.1 inches (e.g., about 0.045 inches). The conductive braid may be in tension between the rigid portion and the radiating portion.

In some aspects, the rigid portion includes a rigid tube that is disposed about the dielectric and that is in electrical communication with the conductive braid. The rigid tube may be in intimate contact with the dielectric to prevent fluid ingress towards a proximal portion of the cable assembly. A proximal end of the inner conductor may extend from the rigid tube. A distal portion of the rigid tube may fix the position of a proximal end of the conductive braid relative to the dielectric. The distal portion of the rigid tube may be flared over a proximal end of the conductive braid of the central portion. The flexible portion may include a tube shrunk over a joint defined between the rigid tube and the conductive braid to seal the joint. The tube shrunk over the joint may also provide strain relief for the joint.

In certain aspects, the radiating portion includes a first step and a second step. The first step may be formed from a first dielectric tube and a second dielectric tube and the second step may be formed from the second dielectric tube. The combined thickness of the first and second dielectric tube may be less than the thickness of the dielectric. The second dielectric tube may extend proximally from the second step to overlap the first dielectric tube and the distal end of the dielectric to seal a first step down between the first step and the dielectric. The second dielectric tube may extend distally from a distal end of the conductive braid. The radiating portion may include a distal tip of the inner conductor that extends from a distal end of the second dielectric tube.

In particular aspects, the conductive braid extends over the first step and the second step. The conductive braid may be tucked against the distal end of the dielectric to form a discrete first step down between the dielectric and the first step. The conductive braid may be tucked against a distal end of the first step to form a discrete second step down between the first and second steps.

In aspects, the conductive braid extends over the second step and the radiating portion includes a choke braid that is disposed about the conductive braid distal of the second step down. A proximal portion of the choke braid may be in electrical communication with the conductive braid. The radiating portion may include a dielectric choke tube that is disposed between the choke braid and the conductive braid that is position distal of the proximal end of the choke braid. The radiating portion may include a third tube that is disposed about the conductive braid and the choke braid. A proximal portion of the third tube may be disposed about the first step and a distal portion of the third tube may be disposed about a portion of the choke tube extending distally from a distal end of the choke braid.

In another aspect of the present disclosure, a method of manufacturing a cable assembly includes drawing a rigid tube over a proximal portion of a dielectric of a coaxial cable, trimming a proximal end of the dielectric, exposing a length of an inner conductor at a distal end of the coaxial cable, forming an radiating portion about the exposed length of the inner conductor, and leaving the conductive braid exposed between the rigid tube and the radiating portion such that fluid may impregnate the conductive braid. Forming the radiating portion may tension the conductive braid between the rigid tube and the radiating portion.

In aspects, the method includes verifying a diameter of the dielectric at an end of the coaxial cable before drawing the rigid tube over the proximal portion of the dielectric. The method may include coating a proximal portion of the conductive braid and trimming the proximal end of the conductive braid to leave a coated proximal portion of the conductive braid about the dielectric before drawing the rigid tube over the proximal portion of the dielectric. Drawing the rigid tube over the proximal portion of the dielectric may include positioning the distal end of the rigid tube distally beyond the coated proximal portion of the conductive braid. The method may include flaring the distal portion of the rigid tube before positioning the distal portion of the rigid tube distally beyond the coated proximal portion of the conductive braid.

In some aspects, the method includes measuring a length of the dielectric extending beyond a proximal end of the inner conductor after drawing the rigid tube over the proximal portion of the dielectric to verify a seal is formed between the rigid tube and the dielectric. The method may include sealing a joint between the distal end of the rigid tube and the conductive braid with a shrink tube disposed about the rigid tube and the conductive braid. The method may include reinforcing the proximal portion of the rigid tube before trimming the proximal end of the dielectric. Reinforcing the proximal portion of the rigid tube may include tin tipping the proximal portion of the rigid tube. The method may include sharpening the proximal portion of the inner conductor after trimming the proximal end of the dielectric.

In certain aspects, exposing a length of the inner conductor at the distal portion of the coaxial cable includes laser stripping the dielectric from the inner conductor. Forming the radiating portion about the exposed length of the inner conductor may include shrinking a first dielectric tube over the inner conductor with a proximal end of the first dielectric tube abutting a distal end of the dielectric. Forming the radiating portion may include shrinking a second dielectric tube over the distal end of the dielectric, the first dielectric tube, and a portion of the exposed inner conductor. Wherein forming the radiating portion includes extending the conductive braid over the first and second dielectric tubes, tucking the conductive braid into a joint between the distal end of the dielectric tube and the proximal end of the first dielectric tube to form a first discrete step down and tucking the conductive braid about the distal end of the first dielectric tube to form a second discrete step down.

In particular aspects, forming the radiating portion includes shrinking a choke tube over the conductive braid with a proximal end of the choke tube distally spaced from the second step down. Forming the radiating portion may include positioning a choke braid over the choke tube with a proximal portion of the choke braid extending proximally beyond the proximal end of the choke tube and the distal end of the choke braid proximally spaced from a distal end of the choke tube. Positioning the choke braid over the choke tube may include joining the proximal portion of the choke braid to the conductive braid proximal of the choke tube. Joining the proximal portion of the choke braid to the conductive braid may include soldering the proximal portion of the choke braid to the conductive braid such that the choke braid and the conductive braid are in electrical communication. Forming the radiating portion may include shrinking a third tube over the conductive braid and the choke braid with a proximal end of the third tube positioned about the choke tube distal to the distal end of the choke braid.

In aspects, forming the radiating portion includes trimming a distal end of the conductive braid to expose a portion of the second dielectric tube to form a feedgap of the radiating portion. A distal radiating portion may be connected to the exposed inner conductor beyond a distal end of the second dielectric tube. The distal radiating portion may be soldered to the exposed inner conductor. The distal radiating portion may be abutted to the distal end of the second dielectric tube.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein:

FIG. 10 is a partial perspective view showing the proximal portion of the coaxial cable of FIG. 9 with a portion of the dielectric exposed;

FIG. 11 is a partial perspective view of the end of the coaxial cable of FIG. 10 extending from jaws of a clamping device;

FIG. 12 is a partial perspective view showing the proximal portion of the coaxial cable of FIG. 11 removed from the jaws;

FIG. 13 is a partial side view showing the ends of the coaxial cable of FIG. 12 with a length the dielectric exposed in the connection portion;

DETAILED DESCRIPTION

Figure 1:
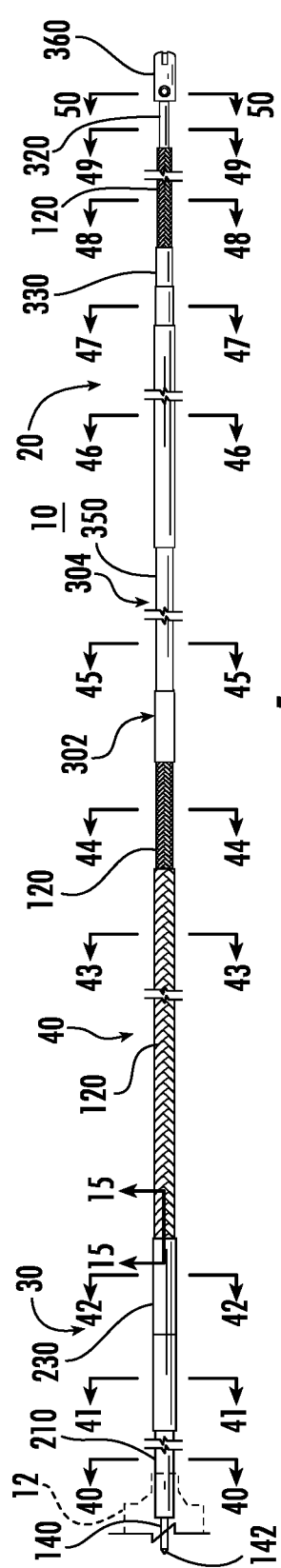
FIG. 1 is a side view of an ablation cable assembly 10 provided in accordance with the present disclosure.

This disclosure relates generally to an ablation cable assembly that includes a water tight semi-rigid proximal portion, a flexible central portion, and a radiating portion. The central portion includes an exposed outer conductor that can be in contact and/or impregnated with fluids such as saline, dielectric fluids, cooling fluids, or bodily fluids. The fluids can be pressurized. As detailed below, the thickness of the outer conductor is minimized to maximize a thickness of a dielectric and an inner conductor for a given diameter of the cable assembly. By maximizing the thickness of the dielectric and the inner conductor the power handling of the ablation cable assembly can be increased such that the radiating portion can continuously deliver at least 150 watts of electrosurgical energy to tissue. In addition, by maximizing the thickness of the dielectric and the inner conductor attenuation for the cable assembly can be reduced. Further, exposing the outer conductor to fluids allows for increased cooling of the ablation cable assembly. The ablation cable assembly is formed from a plurality of dielectric tubes that overlap one another at joints between the tubes to prevent fluid from contacting an inner conductor of the ablation cable assembly.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician.

Figure 3:
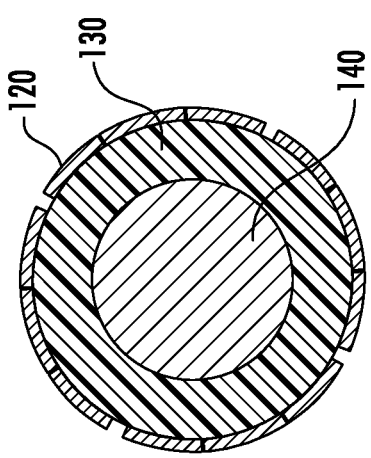
FIG. 3 is a cross-sectional view taken along section line 3-3 of FIG. 2.

With reference to FIG. 1, an exemplary ablation cable assembly 10 is shown in accordance with the present disclosure. The ablation catheter assembly 10 includes a radiating portion 20, a rigid or connection portion 30, and a central portion 40 between the radiating portion 20 and the connection portion 30. The radiating portion 20 is formed to inhibit fluid ingress between a dielectric 130 and an inner conductor 140 (FIG. 3). In addition, the radiating portion 20 precisely positions conductor and dielectric segments, maintains critical dimensional tolerances, and is flexible. The connection portion 30 inhibits fluid ingress about the inner conductor 140 and is rigid or semi-rigid to assist in navigation of the radiating portion 20. The ablation catheter assembly 10 may have an overall diameter of about 2 mm which would be suitable for continuously delivery 150 watts of electrosurgical energy to tissue in connection with a bronchoscopic navigation system (not shown). Experimentation has shown that ablation catheter assemblies of the construction disclosed herein can have a diameter of less than 2 mm and continuously deliver 150 watts of electrosurgical energy to tissue. For an example of a bronchoscopic navigational system and uses thereof reference can be made to U.S. patent application Ser. No. 14/753,229, filed Jun. 29, 2015, the entire contents of which are herein incorporated by reference.

Referring to FIGS. 2-39, the construction and a method of manufacturing the ablation catheter assembly 10 is described in accordance with the present disclosure. Specifically, the construction of the radiating portion 20 and the connection portion 30 from a flexible coaxial cable 100 will be described.

Figure 2:
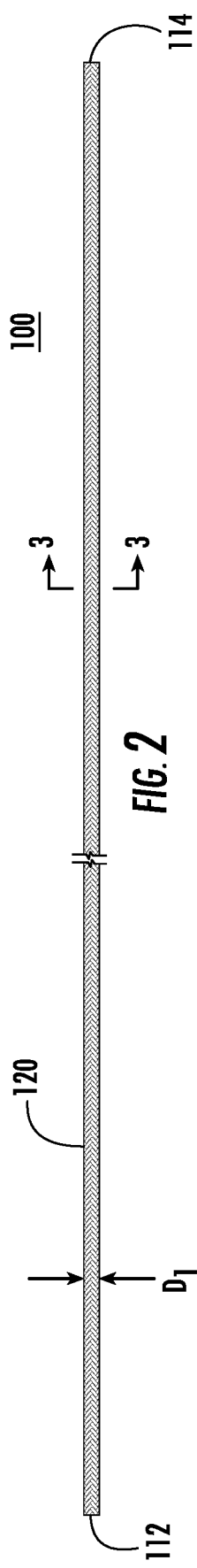
FIG. 2 is a side view of coaxial cable forming a portion of the ablation cable assembly 10 of FIG. 1.

Initially, referring to FIGS. 2 and 3, a flexible coaxial cable 100 is provided having an outer diameter $D_1$ and a length $L_1$. The outer diameter $D_1$ is in a range of about 0.0300 inches to about 0.0500 inches (e.g., about 0.04 inches) and the length $L_1$ is in a range of about 10 inches to about 60 inches (e.g., about 12 inches). It will be appreciated that if the length of the coaxial cable 100 is greater than a desired length $L_1$, the coaxial cable 100 may be cut to a desired length $L_1$.

The coaxial cable 100 is flexible and has an outer conductive braid 120, a dielectric 130 disposed within the braid 120, and an inner conductor 140 disposed within the dielectric 130. The diameter of the inner conductor 140 and the thickness of the dielectric 130 are maximized and the thickness of the conductive outer braid 120 is minimized. The inner conductor 140 is formed of a solid conductive material (e.g., copper, stainless steel, silver, gold, or platinum) and the dielectric 130 is formed from a solid insulative material (e.g., polytetrafluoroethylene (PTFE)). The dielectric 130 may be transparent or translucent. The conductive outer braid 120 is formed from a weave of flat wire stock which reduces the thickness of the conductive outer braid 120 and permits fluids to penetrate or impregnate the conductive outer braid 120. It will be appreciated that by forming the conductive outer braid 120 from flat wire stock reduces the thickness of the conductive outer braid 120 when compared to braids formed from rounded wire stock. The conductive outer braid 120 may also be formed of any conductive material including copper, silver, gold, or platinum, though stainless steel is commonly used.

Figure 6:
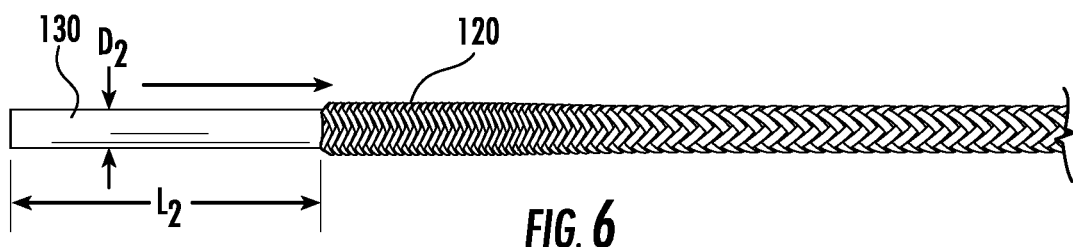
FIG. 6 is a side view of the proximal portion of the coaxial cable of FIG. 2 with a braid compressed to expose a dielectric of the coaxial cable.

As shown in FIG. 6, the braid 120 is pushed back at a first end 112 from over the dielectric 130 of the coaxial cable 100 to expose a length $L_2$ of the dielectric 130. The exposed length $L_2$ of the dielectric 130 maybe in a range of about 1 inch to about 4 inches (e.g., about 3 inches). The exposed length $L_2$ of the dielectric 130 is measured to verify that the diameter $D_2$ of the dielectric 130 is greater than a minimum acceptable diameter. The minimum acceptable diameter of the dielectric 130 is determined by a required power output of the radiating portion 20 (FIG. 1) and materials of the dielectric 130 and the inner conductor 140. It is appreciated that the inner conductor 140 is disposed within the dielectric 130. For example, when the dielectric 130 is made of PTFE, the inner conductor 140 may be a solid copper wire, and the required power output of the ablation catheter assembly 10 may be up to about 150 W, the minimum required diameter of the dielectric 130 is in a range of about 0.017 inches to about 0.490 inches (e.g., about 0.036 inches). The inner conductor may be made from solid copper wire, copper clad steel, silver plated copper clad steel, steel, solid silver wire, or other suitable conductive materials.

A tool (e.g., a micrometer or a die (not shown)) is used to measure the diameter $D_2$ of the dielectric 130. If the diameter $D_2$ of the dielectric 130 at the first end 112 of the coaxial cable 100 is less than the minimum required diameter of the dielectric 130, the dielectric 130 at the other or second end 114 of the coaxial cable 100 is checked by pushing back the braid 120 and measuring the diameter $D_2$ of the dielectric 130 at the second end 114 is performed. If the diameter $D_2$ of the dielectric 130 of the first and second ends 112, 114 of the coaxial cable 100 are less than the minimum required diameter of the dielectric 130, the coaxial cable 100 is discarded and the preceding steps are repeated until the diameter $D_2$ of the dielectric 130 of one of the first or second ends 112, 114 of the coaxial cable 100 is greater than or equal to the minimum required diameter of the dielectric 130. Only the dielectric 130 at the first end 112 of the coaxial cable 100 is required to have a diameter $D_2$ greater than or equal to the minimum required diameter, thus, if the first end 112 has a diameter less than the minimum required diameter and the second end 114 has a diameter equal to or greater than the minimum required diameter the first and second ends 112, 114 of the coaxial cable 100 can be swapped. The first end 112 has an end 142 of the inner conductor 140 and the second end 114 has an end 144 of the inner conductor 140. It will be appreciated that the dielectric 130 at the radiating portion 20 may have a diameter greater or less than the minimum required diameter of the dielectric 130.

Figure 7:
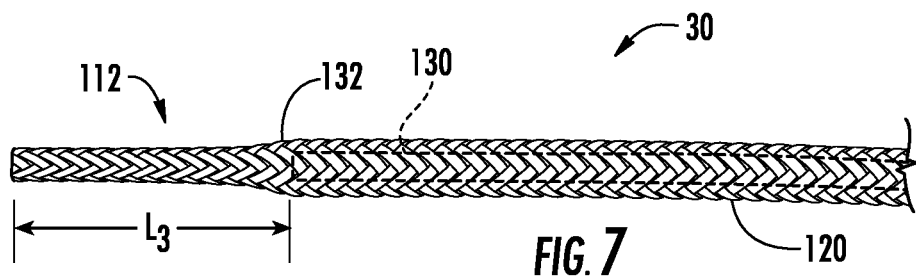
FIG. 7 is a side view of the proximal portion of coaxial cable of FIG. 6 with the braid pulled over an end of the dielectric.

Referring now to FIG. 7, in the first step in forming the connection portion 30 the braid 120 drawn over an end 132 of the dielectric 130 a length $L_3$ and the braid 120 is positioned flush with the end 134 (FIG. 18) of the dielectric 130 at the second end 114 of the coaxial cable 100 (FIG. 2). The length $L_3$ can be any length as the first end 112 can be trimmed as detailed below; however, it is contemplated that the length $L_3$ is in a range of about 0.125 inches to about 0.375 inches (e.g., about 0.25 inches).

Figure 8:
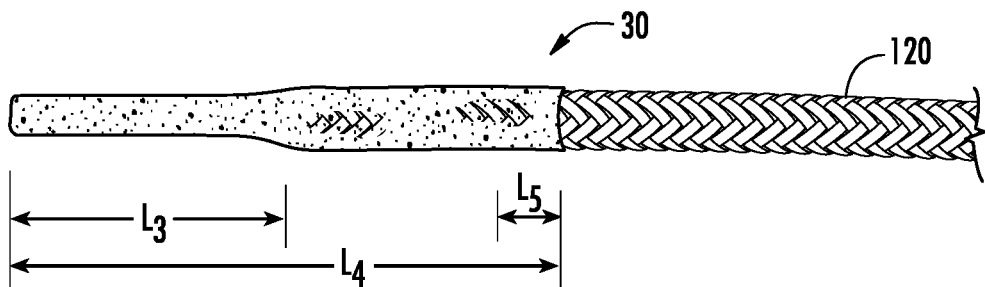
FIG. 8 is a side view of the coaxial cable of FIG. 7 with an end of the braid plated.

With reference to FIG. 8, a length $L_4$ of the connection portion 30 is coated or plated. For example, the length $L_4$ can be tin-dipped in a solder (e.g., SN96 lead-free solder). The length $L_4$ is approximately twice the length $L_3$. Similar to the length $L_3$, the length $L_4$ can be any length as the first end 112 can be trimmed as detailed below; however, it is contemplated that the length $L_4$ is in a range of about 0.25 inches to about 0.75 inches (e.g., about 0.5 inches). Tin dipping of the length $L_4$ of the connection portion 30 may include inserting the length $L_4$ of the connection portion 30 into liquefied solder in approximately 1 second and removing the length $L_4$ of the connection portion 30 from the liquefied solder in approximately 1 second without allowing the length $L_4$ of the connection portion 30 to dwell within the liquefied solder between the inserting and removing of the length $L_4$ of the connection portion 30.

Figure 9:
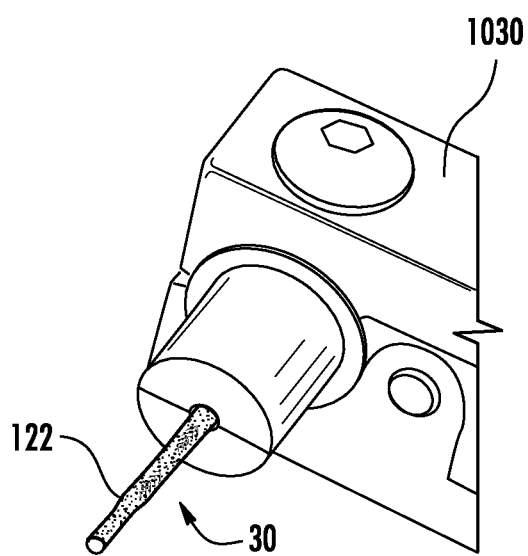
FIG. 9 is a partial perspective view of an end of the coaxial cable of FIG. 8 extending from jaws of a clamping device.

Referring to FIG. 9, the coated length $L_4$ of the connection portion 30 is positioned in a clamp 1030 which holds the connection portion 30 with the coated length $L_4$ of the connection portion 30 extending from the jaws 1030. A length $L_5$ (FIG. 8) of the coated length $L_4$ of the connection portion 30 is positioned within the jaws 1030 with the remainder of the coated length $L_4$ of the connection portion 30 extending from the jaws 1030. The length $L_5$ can be in a range of about 0.01 inches to about 2 inches or in a range of about 0.02 inches to about 0.05 inches (e.g., about 0.035 inches). With the length $L_5$ of the coated length $L_4$ of the connection portion 30 positioned within the jaws 1030, a cutting tool (e.g., a razor blade (not shown)) is used to trim and remove the portion 122 of the braid 120 extending from the jaws 1030 without cutting the dielectric 130. Trimming the braid 120 leaves the length $L_5$ of the coated length $L_4$ of the braid 120 with a first end 132 of the dielectric 130 exposed as shown in FIG. 10. The coated length $L_5$ of the braid 120 prevents the end of the braid 120 from unraveling or fraying.

With reference to FIG. 11, the connection portion 30 is repositioned within the jaws 1030 such that a length $L_6$ of the braid 120 is exposed from the jaws 1030. The length $L_6$ includes the coated length $L_5$ and is in a range of about 0.04 inches to about 0.07 inches (e.g., about 0.055 inches). With the length $L_6$ exposed from the jaws 1030, a marking tool (e.g., permanent marker (not shown)) is used to create a mark 125 about the braid 120 to indicate the length $L_6$ without damaging the braid 120 as shown in FIG. 12.

Referring now to FIG. 13, the connection portion 30 is removed from the jaws 1030 and the braid 120 is retracted to expose a length $L_7$ of the dielectric 130 at the connection portion 30. This is possible in part because the solder used for the tin dipping process does not permanently adhere to the PTFE of the dielectric 130. The length $L_7$ is in a range of about 2 inches to about 12 inches (e.g., about 4 inches). As the braid 120 is retracted from over the connection portion 30, the braid 120 is tightened or "milked" from the connection portion 30 towards the radiating portion 20 (FIG. 1) such that the braid 120 is smooth along the length of the coaxial cable 100. When the braid 120 is smooth and the length $L_7$ of the dielectric 130 is exposed at the connection portion 30, a portion of the braid 120 is trimmed at the radiating portion 20 such that the braid 120 extends beyond the dielectric 130 at the radiating portion 20 (i.e., over the end 144 of the inner conductor 140). The braid 120 can extend beyond the dielectric 130 can be any length; however it is contemplated that this position of the braid 120 has a length of about 0.05 inches to about 10 inches (e.g., about 0.5 inches). The portion 126 of the braid 120 may discarded or saved for creation of a choke braid 340 (FIG. 29) for the radiating portion 20 as detailed below.

Figure 14:
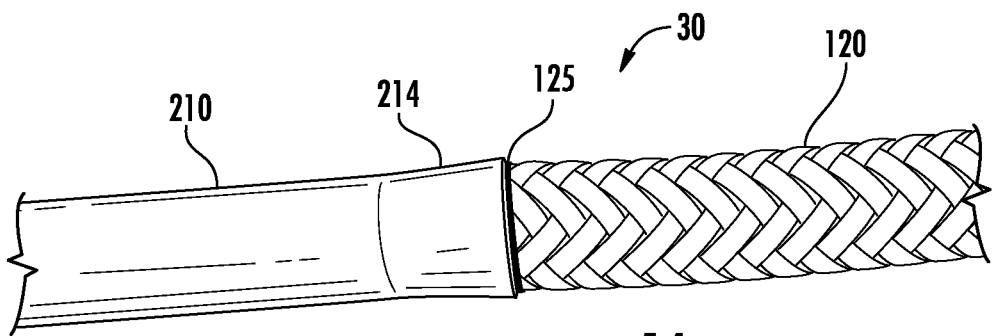
FIG. 14 is a partial side view showing a copper tube disposed over the connection portion of FIG. 13.
Figure 15:
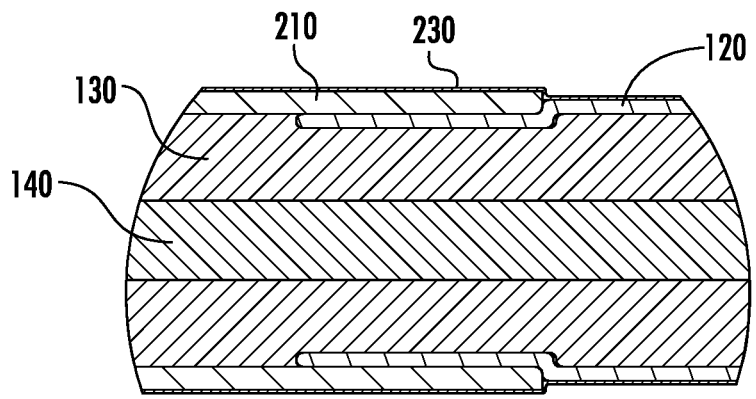
FIG. 15 is a cross-section taken along section line 15-15 of FIG. 1.

With reference to FIG. 14, a rigid tube 210 is provided having an inner diameter which is approximately equal to the diameter $D_1$ of the coaxial cable 100 (i.e., the outer diameter of the braid 120). The outer diameter of the rigid tube 210 is in a range of about 0.03 inches to about 0.04 inches (e.g., about 0.0319 inches or about 0.0331 inches). The rigid tube 210 is formed of a conductive material or be constructed from a base material and plated with a different and highly conductive material. For example, the rigid tube 210 may be formed entirely from copper or may be constructed from stainless steel and plated with copper, silver, or gold. By using a base material a material having a different stiffness than the plating material may be advantageously utilized.

Initially, an end portion 214 of the rigid tube 210 is flared such that the end portion 214 will fit over the coated length $L_5$ of the braid 120 to the mark 125. A flaring tool (not shown) may be used to flare the end portion 214 of the rigid tube 210. With the end portion 214 of the rigid tube 210 flared, the rigid tube 210 is slid over the length $L_7$ of the dielectric 130 such that the flared end portion 214 of the rigid tube 210 is positioned at the mark 125 as shown in FIG. 14 (i.e., the flared end portion 214 is over about half of the mark 125). While sliding the rigid tube 210 over the length $L_7$ of the dielectric 130, the braid 120 and the dielectric 130 are held beyond the mark 125 to prevent the braid 120 from sliding relative to the dielectric 130 such that the length $L_7$ remains constant. In addition, the rigid tube 210 may be rotated as it is slid over the length $L_7$ to assist in the positioning of the end portion 214 of the rigid tube 210 at the mark 125.

Figure 16:
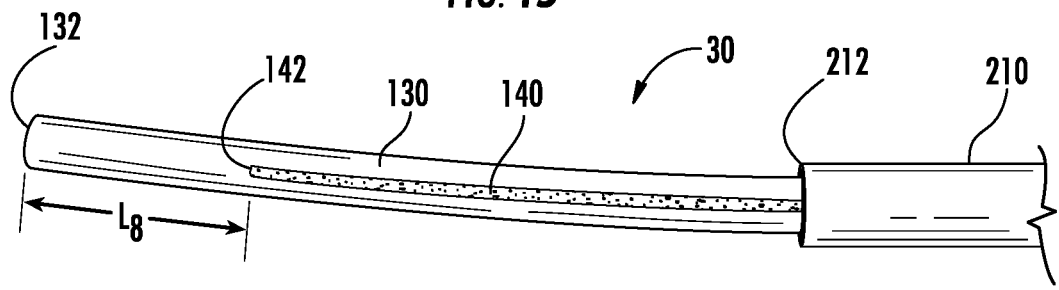
FIG. 16 is a partial side view showing a portion of the copper tube of FIG. 14.

When the end portion 214 of the rigid tube 210 is positioned at the mark 125, the rigid tube 210 is drawn down over the braid 120 and the dielectric 130 from the flared end portion 214 of the rigid tube 210 towards a distal end 212 of the rigid tube 210 such that the end portion 214 of the rigid tube 210 secures the coated length $L_5$ (FIG. 12) of the braid 120 to the dielectric 130. Drawing down the rigid tube 210 over the dielectric 130 compresses and extrudes a portion of the dielectric 130 over the end 142 of the inner conductor 140 as shown in FIG. 16 such that an end 132 of the dielectric 130 extends proximally over the end 142 of the inner conductor 140 a length $L_8$. The length $L_8$ has a minimum distance of about 0.020 inches to ensure that the rigid tube 210 is drawn tightly over the dielectric 130 (i.e., is in intimate contact with the dielectric 130) to form a water tight seal between the rigid tube 210 and the dielectric 130. If the length $L_8$ is less than 0.020 inches the coaxial cable 100 may be discarded. In addition, if the end 142 of the inner conductor 144 does not extend from the end 212 of the rigid tube 210, the coaxial cable 100 is discarded. It will be appreciated that during the drawing of the rigid tube 210, the end 134 of the dielectric 130 remains flush with the end 144 of the inner conductor 140.

Figure 17:
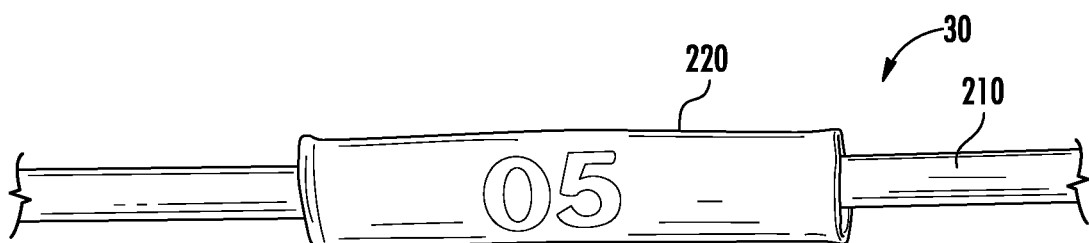
FIG. 17 is a partial side view showing a sleeve disposed over the copper tube of FIG. 14.

Further, after the rigid tube 210 is drawn over the dielectric 130, a sleeve 220 may be slid over the rigid tube 210 to identify the catheter assembly 10 (FIG. 1) as shown in FIG. 17. The sleeve 220 may be preshrunk such that the sleeve 220 fits snugly over the rigid tube 210. The sleeve 220 may be preprinted with identifying indicia (e.g., all or a portion of a serial number or an RFID tag) of the final catheter assembly 10. Alternatively, before or after the rigid tube 210 is drawn down, the rigid tube 210 can be etched or labeled with identifying indicia of the final catheter assembly 10. It will be appreciated that the sleeve 220 may be a temporary identification member that is used to identify the catheter assembly 10 during manufacturing and may be removed during or after the manufacturing process.

Figure 18:
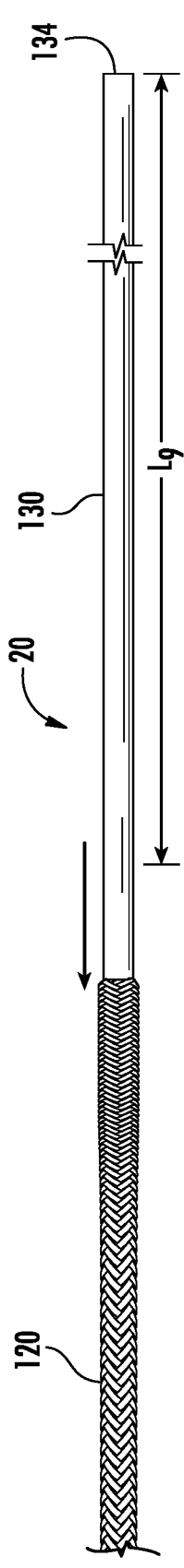
FIG. 18 is a partial side view of the distal portion of the coaxial cable of FIG. 2 with the braid compressed to expose the dielectric.
Figure 19:
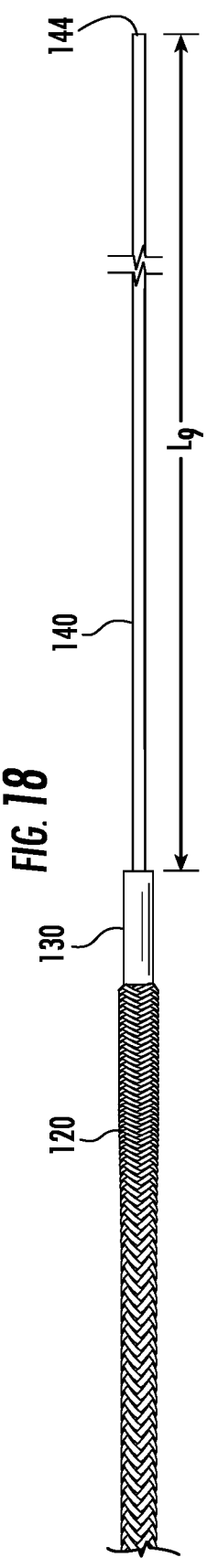
FIG. 19 is a partial side view showing the distal portion of the coaxial cable of FIG. 18 with the dielectric stripped from over a portion of an inner conductor.

Referring now to FIGS. 18-36, with the rigid tube 210 fixing the braid 120 to the dielectric 130, the assembly of the remainder of the catheter assembly 10 including the radiating portion 20 is performed in accordance with the present disclosure. Initially as detailed above, the braid 120 was trimmed to leave the braid 120 extending over the end 134 of the dielectric 130. The braid 120 is now pulled back over the dielectric 130 (i.e., towards the connection portion 30 and the rigid tube 210) to expose a length $L_9$ of the dielectric 130 as shown in FIG. 18. The length $L_9$ can be in a range of about 2 inches to about 15 inches or in a range of about 5 inches to about 8 inches (e.g., about 6 inches). The length $L_9$ of the dielectric 130 is then removed or stripped to expose the inner conductor 140 along the length $L_9$ as shown in FIG. 19. It is contemplated that any known means of stripping the length $L_9$ of the dielectric 130 may be used including, but not limited to, laser stripping.

Figure 20:
FIG. 20 is a partial side view showing the distal portion of the coaxial cable of FIG. 19 with a first tube disposed about the inner conductor.

Referring now to FIG. 20, a first shrink tube 310 is slid over the end 144 of the inner conductor 140 until an end 312 of the first shrink tube 310 abuts the dielectric 130. The first shrink tube 310 has a length $L_{10}$ which can be in a range of about 0.2 inches to about 3 inches or in a range of 0.7 inches to about 0.9 inches (e.g., about 0.8 inches). The first shrink tube 310 forms a "first step 302" of the completed cable assembly 10 (FIG. 1). It will be appreciated that the length $L_{10}$ may be adjusted such that the total length of the first step 302 of the cable assembly 10 is in a range of about 0.2 inches to about 5 inches or in a range of about 0.8 inches to about 0.86 inches (e.g., about 0.83 inches) as detailed below. With the first shrink tube 310 abutting the dielectric 130, the first shrink tube 310 is shrunk over the inner conductor 140 from the proximal end 312 of the first shrink tube 310 to a distal end 314 of the first shrink tube 310. To ensure that after shrinking the first shrink tube 310 is in an abutting relationship with the dielectric 130 (i.e., that there is no gap between the first shrink tube 310 and the dielectric 130), an initial length (e.g., about 0.25 inches) of the first shrink tube 310 may be shrunk and the abutting relationship verified before shrinking the remainder of the first shrink tube 310. If there is a gap between the first shrink tube 310 and the dielectric 130 after the initial length is shrunk, the end 312 of the first shrink tube 310 may be slid into an abutting relationship before shrinking the remainder of the first shrink tube 310.

The first shrink tube 310 may be formed from PTFE. To shrink the first shrink tube 310, a hot box (not shown) may be used to heat the first shrink tube 310 to a temperature in a range about 650° F. to about 800° F. (e.g., about 750° F.) to shrink the first shrink tube 310.

Figure 21:
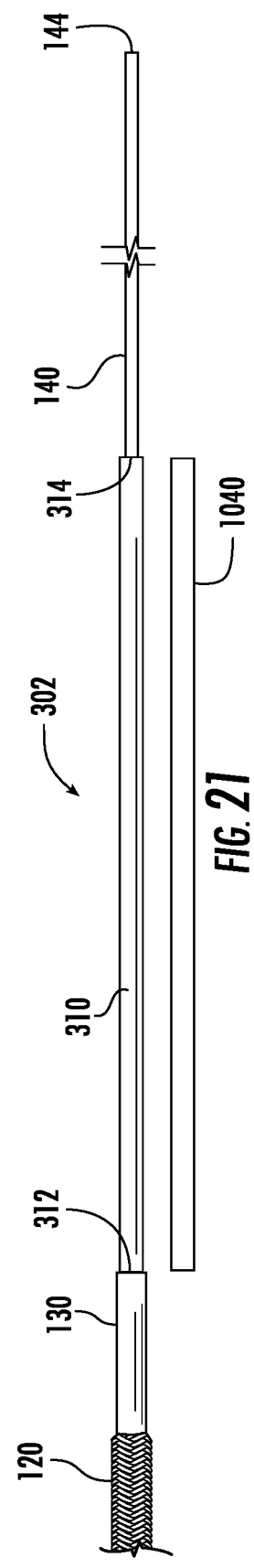
FIG. 21 is a partial side view of the first tube in an abutting relationship with the dielectric of the coaxial cable of FIG. 20.

With reference to FIG. 21, after the first shrink tube 310 is shrunk, a tool (e.g., jig 1040) is used to determine that the shrunk length of the first shrink tube 310 (i.e., the first step 302) is within an acceptable range. It will be appreciated that during shrinking of the first shrink tube 310, the length of the first shrink tube 310 may increase. The jig 1040 has a length equal to a desired length of the first step 302 as detailed above. It is contemplated that a first jig may be used having a length equal to a minimum length for the first step 302 and a second jig may be used having a length equal to a maximum length of the first step 302. If the shrunk length of the first shrink tube 310 is less than the minimum length of the first step 302, the coaxial cable 100 is discarded. If the shrunk length of the first shrink tube 310 is greater than the maximum length of the first step 302, the shrunk first shrink tube 310 may be trimmed to a desired length of the first step 302 as detailed above.

Figure 22:
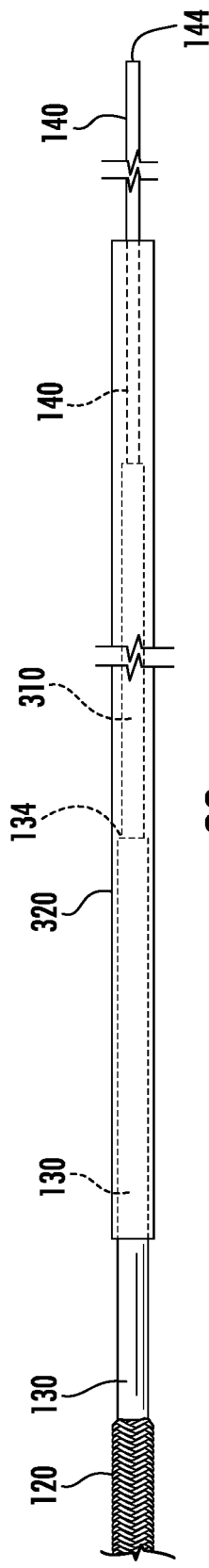
FIG. 22 is a partial side view of a second tube disposed over the first tube of FIG. 21.
Figure 23:
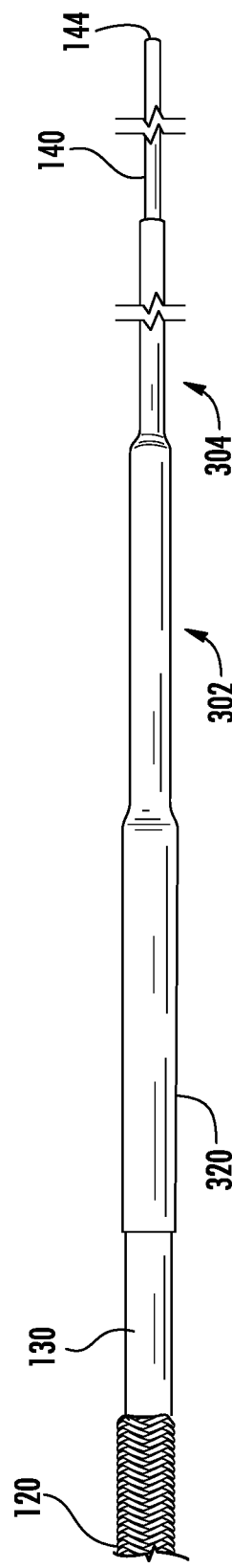
FIG. 23 is a partial side view of the second tube shrunk over the dielectric, the first tube, and the inner conductor of FIG. 22.

Referring now to FIG. 22, with the length of the first step 302 verified to be within the acceptable range, a second shrink tube 320 is slid over the end 144 of the inner conductor 140, over the shrunk first shrink tube 320, and over about 1 inch of the end 134 of the dielectric 130. The second shrink tube 320 has a length of about 4 inches and may be formed from PTFE. With the second shrink tube 320 slid over the about 1 inch of the end 134 of the dielectric 130, the second shrink tube 320 is shrunk over about the 1 inch of the end 134 of the dielectric 130, the shrunk first shrink tube 130 (i.e., the first step 302), and a portion of the inner conductor 140 as shown in FIG. 23. To shrink the second shrink tube 320, a hot box (not shown) may be used to heat the second shrink tube 320 to a temperature in a range about 650° F. to about 800° F. (e.g., about 750° F.). It will be appreciated that the second shrink tube 320 is shrunk from the end of the second shrink tube 320 slid over the dielectric 130 towards the end 144 of the inner conductor 140. After the second shrink tube 320 is shrunk, the second shrink tube 320 is checked to verify that no air bubbles are present within the second shrink tube 320. If air bubbles are present within the second shrink tube 320, the second shrink tube 320 may be reheated to eliminate the air bubbles. If the air bubbles remain after the reheating of the second shrink tube 320, the coaxial cable 100 may be discarded. The portion of the second shrink tube 320 extending distally beyond the first step 302 and over the inner conductor 140 forms the second step 304 of the cable assembly 10 (FIG. 1). It will be appreciated that the second shrink tube 320 seals the abutting connection between the dielectric 130 and the first shrink tube 310 and forms a seal about the inner conductor 140.

After the second step 304 of the cable assembly 10 is formed, critical values may be verified (e.g., the diameter of the braid 120 proximal to the first step 302, the diameter and length of the first step 302, the diameter and the length of the second step 304). Specialized equipment (e.g., a lighted microscope) may be required for accurately measuring critical values of the cable assembly 10.

Figure 24:
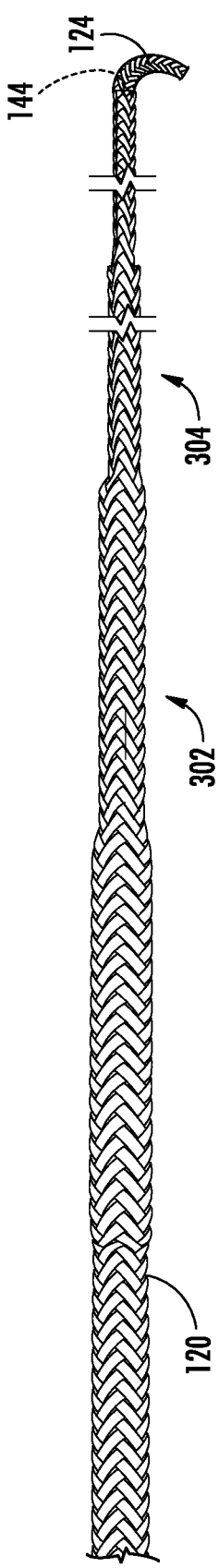
FIG. 24 is a partial side view showing the distal portion of the coaxial cable of FIG. 23 with the braid extended past the distal end of the inner conductor.

After the second step 304 of the cable assembly 10 is formed and the critical values are recorded, the braid 120 is tightened from the connection portion 30, over the first and second steps 302, 304, and over the end 144 of the inner conductor 140 to remove any voids between the braid 120 and the dielectric 130, the first step 302, and the second step 304 as shown in FIG. 24. It will be appreciated that as the proximal end of the braid 120 is secured in position about the dielectric 130 by the drawn copper tube 120 as detailed above, tightening the braid 120 may induce tension in the braid 120. In addition, tightening the braid 120 ensures that braid 120 has a minimum thickness over the dielectric 130.

Figure 25:
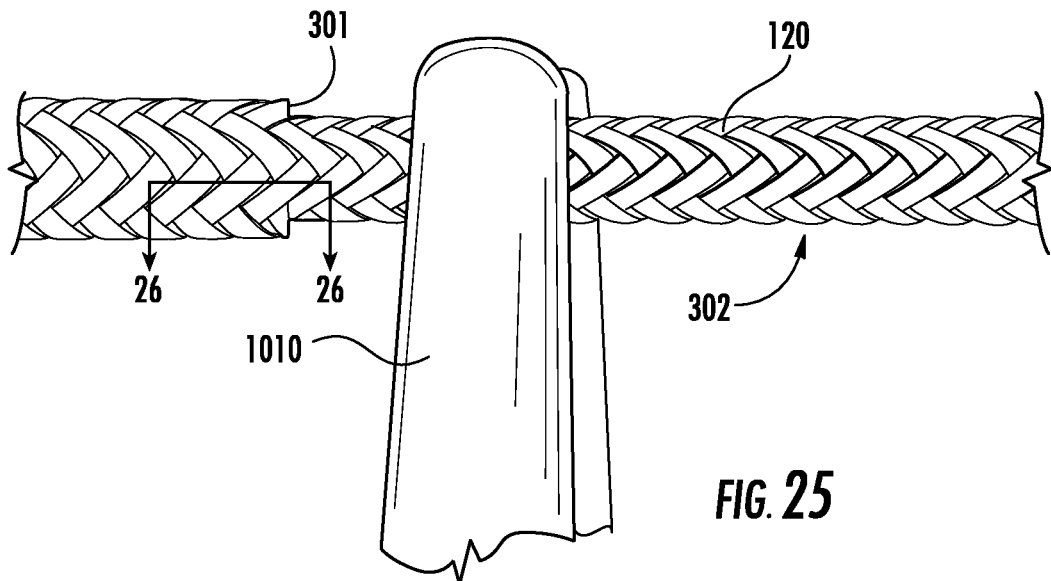
FIG. 25 is an enlarged partial view of the coaxial cable of FIG. 24 illustrating the transition between the dielectric and the first step down of a distal radiator portion of the coaxial cable.
Figure 26:
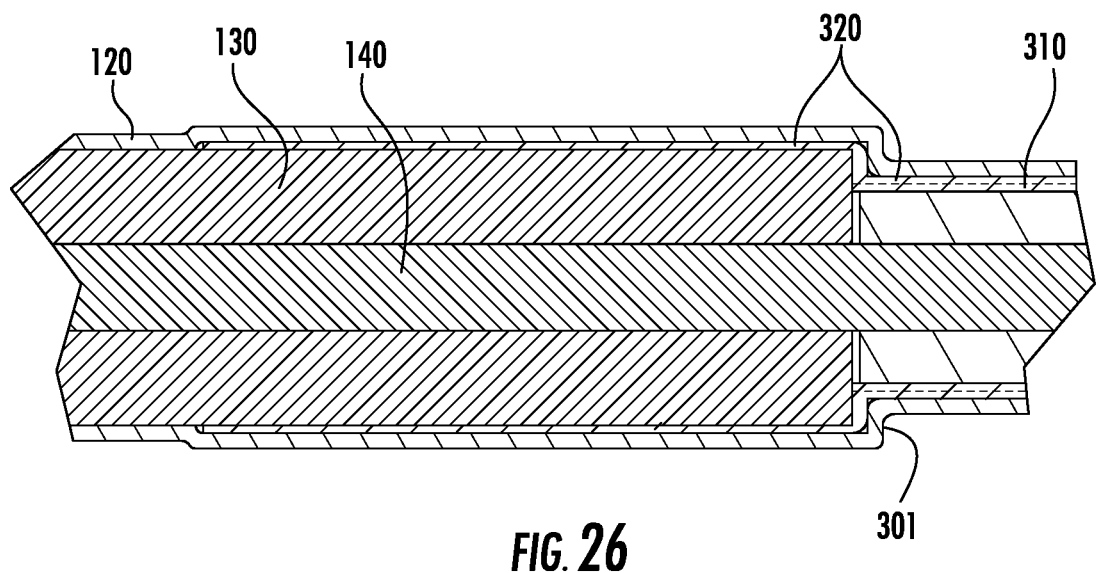
FIG. 26 is a cross-sectional view taken along section line 26-26 of FIG. 25 illustrating a first step down.
Figure 29:
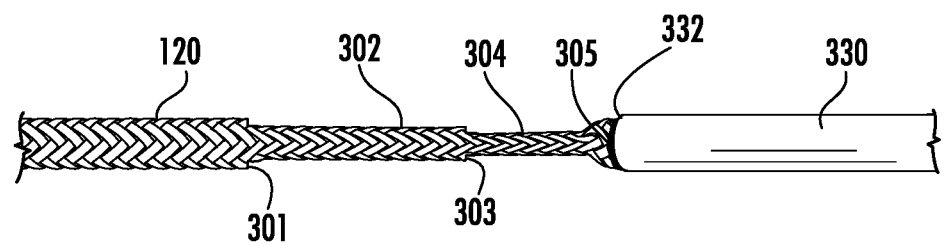
FIG. 29 is a partial side view of the choke tube shrunk over the second step down of the distal radiator portion.

As depicted in FIG. 25 after the braid 120 is tightened over the end 144 of the inner conductor 140, a portion of an end 124 of the braid 120 may be folded over the end 144 of the inner conductor 140 to keep the braid 120 taut. With the braid 120 taut, a tool (e.g., pliers 1010) is used to lightly crimp or tuck the braid 120 around the first step 302 to form a first discrete step down 301, as shown in FIG. 26. Similarly, the braid 120 is tucked around the second step to form a second discrete step down 303 (FIG. 29). Tucking the braid 120 at the first and second step downs 302, 304 keeps tension in the braid 120 and prevents voids from forming between the braid 120 and the dielectric 130, the first step 302, and the second step 304. Preventing voids from forming can assist in maintaining a consistent electrical performance by reducing or eliminating fluid pockets between the braid 120 and the dielectric 130.

Figure 27:
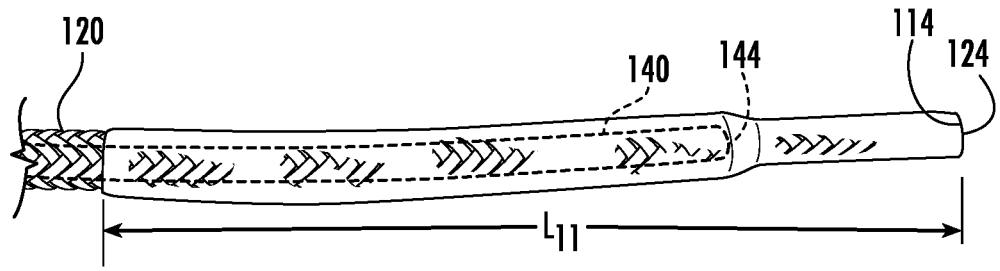
FIG. 27 is a partial side view of a tin-dipped distal portion of the coaxial cable.

Referring now to FIG. 27, the end 124 of the braid 120 is coated a length $L_{11}$ which can be in a range of about 0.1 inches to about 3 inches or in a range of about 0.2 inches to about 0.6 inches (e.g., about 0.4 inches). As shown, the end 124 of braid 120 is tin-dipped such that the end 144 of the inner conductor 140 is within the coated length $L_{11}$. The length $L_{11}$ does not extend to the second step 304. After the length $L_{11}$ is coated, the end 124 of the braid 120 may be trimmed such that about 0.125 inches of the braid 120 extends past the end 144 of the inner conductor 140.

Figure 28:
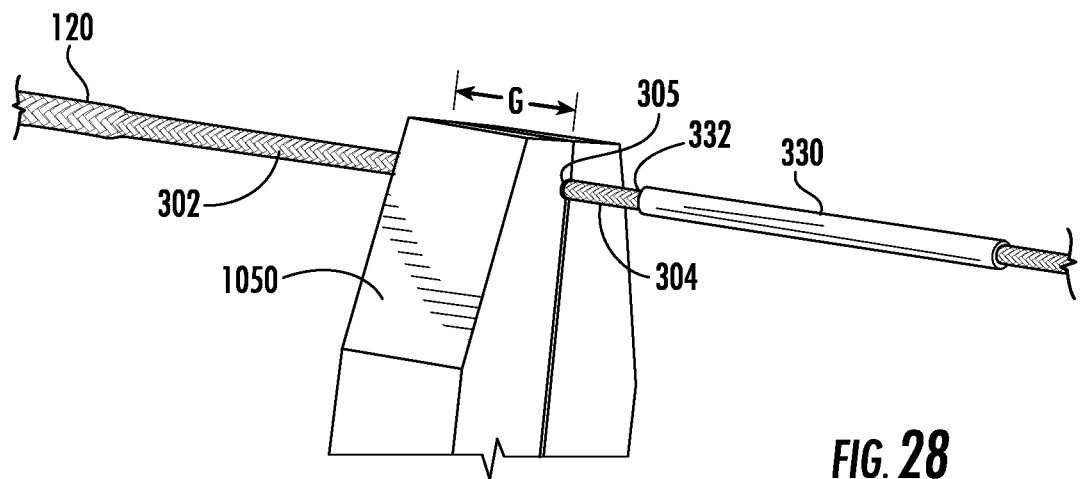
FIG. 28 is a partial perspective view of a gap tool positioned about a second step down of the coaxial cable and a third tube disposed over the braid of the distal portion of the coaxial cable.

With reference to FIG. 28, a gap tool (e.g., pliers 1050) is used to set a gap to position a choke tube 330, formed from PTFE, relative to the first step 302. The pliers 1050 have a width equal to a desired gap G for positioning the choke tube 330 about the second step 304 between the second step down 303 and the distal end of the second step 304. To set the desired gap G for the choke tube 330, the pliers 1050 is positioned on the second step 304 with one side abutting the end of the first step 302. With the pliers 1050 positioned on the second step 304, a mark 305 can be made with a marking tool (e.g., a permanent marker) on the braid 120 before releasing the second step 304 from the pliers 1050. The choke tube 330 is then slid over the second end 114 of the radiating portion 20 until an end 332 of the choke tube 330 is positioned at the mark 305 as shown in FIG. 29. When the end 332 of the choke tube 330 is positioned at the mark 305, the choke tube 330 is shrunk over the second step 304 from the mark 305 towards the end 124 of the braid 120.

To shrink the choke tube 330, an initial portion of the choke tube 330 adjacent the mark 305 may be heated in a hot box to about 650° to about 800° (e.g., about 750°). When the initial portion of the choke tube 330 is shrunk, the position of the end 332 of the choke tube 330 is verified to be at the mark 305 before shrinking the remainder of the choke tube 330. If the end 332 of the choke tube 330 is not at the mark 305, the choke tube 330 is slid over the second step 304 to position the end 332 of the choke tube 330 at the mark 305.

Alternatively, instead of marking the second step 304, the end 332 of the choke tube 330 may be slid over the end 124 of the braid 120 with the pliers 1050 positioned on the second step 304 until the end 332 abuts the pliers 1050. With the end 332 abutting the pliers 1050, the choke tube 330 is heated to shrink the choke tube 330 over the second step 304. It will be appreciated that the pliers 1050 will set the desired gap G between the end 332 of the choke tube 330 and the first step 302.

After shrinking of the choke tube 330, the desired gap G may be verified. If the gap G is outside an acceptable range, the coaxial cable 100 is discarded. Specialized equipment (e.g., a lighted microscope) may be required for accurately measuring the gap G.

Figure 4:
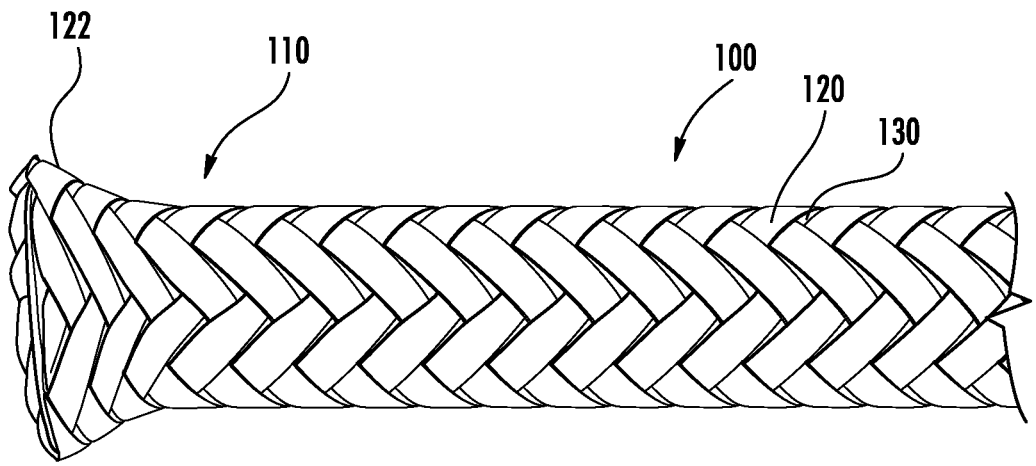
FIG. 4 is an enlarged view of an end portion of the coaxial cable of FIG. 2.
Figure 5:
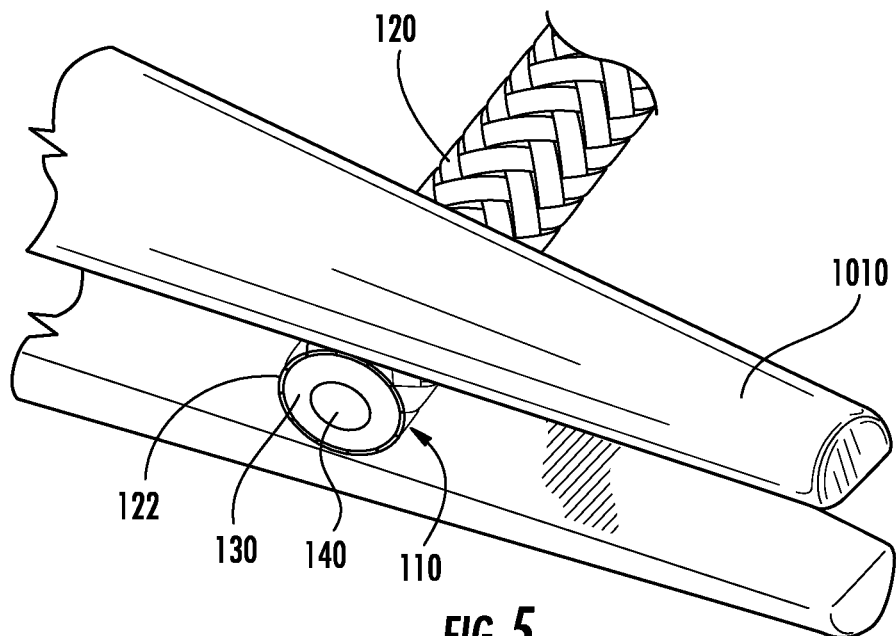
FIG. 5 is a perspective view of a tool engaged with the end of the coaxial cable of FIG. 4.
Figure 30:
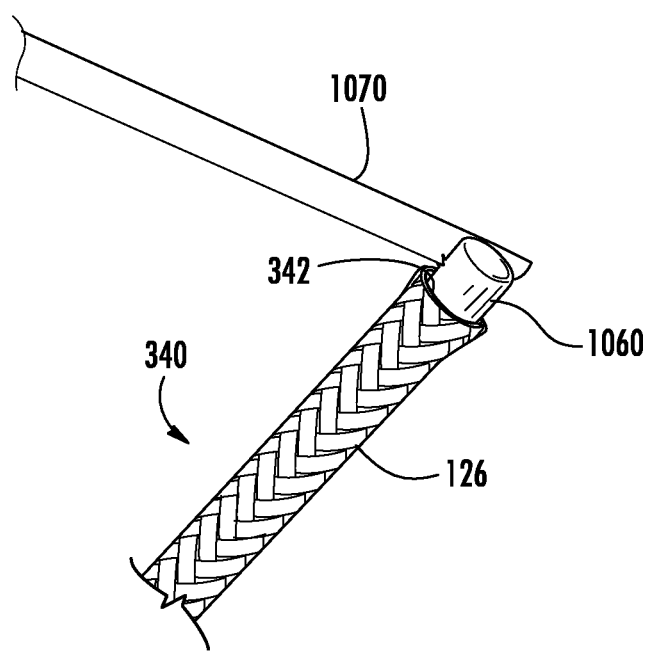
FIG. 30 is a partial perspective view of a pin enlarging a diameter of a choke braid.
Figure 31:
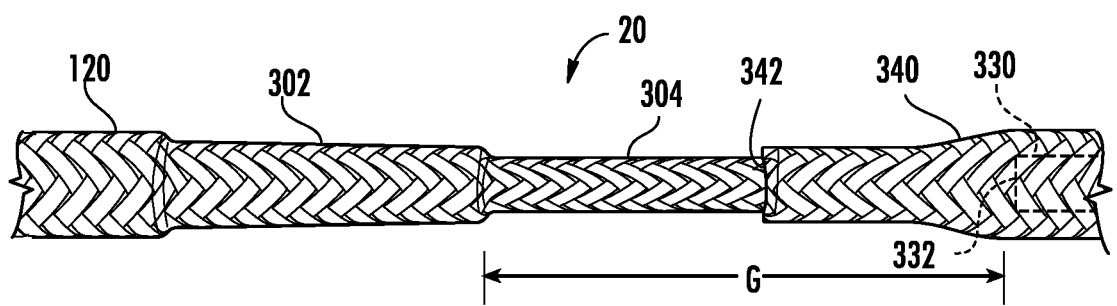
FIG. 31 is a partial side view of the choke braid disposed over the radiator portion with a first end of the choke braid positioned over the second step down.

With reference to FIGS. 30-31, a choke braid 340 is disposed over a portion of the radiating portion 20. The choke braid 340 may be made from the portion 126 of the braid 120 that was discarded above. Alternatively, a piece of coaxial cable may be cut and the outer braid removed to form the choke braid 340. The choke braid 340 can have a length in a range of about 1 inch to about 7 inches or in a range of about 2 inches to about 3 inches (e.g., about 2.5 inches). Referring briefly back to FIGS. 4 and 5, ends of the choke braid 340 are inspected to check if the ends 342, 344 were deformed during cutting to form wings. If a wing was formed during cutting, one or both of the ends of the choke braid 340 are returned to round as detailed above.

With the ends 342, 344 rounded, a tool (e.g., pin 1060) is inserted through the choke braid 340 to open up or enlarge the choke braid 340. The tool may have a diameter of about 0.040 inches. With the pin 1060 disposed within the choke braid 340, a tool (e.g., razor blade 1070) is used to trim end 342 of the choke braid 340 to square and clean the end of 342 of the choke braid 340 as shown in FIG. 30. The pin 1060 may be slid through the choke braid 340 to slightly increase an inner diameter of the choke braid 340 to allow the choke braid 340 to slide over the choke tube 330 as detailed below.

Referring to FIG. 31, the end 342 of the choke braid 340 is slid over the second end 114 of the radiating portion 20 until the end 342 is positioned past the end 332 of the choke tube 330 in a range of about 0.01 inches to about 3 inches (e.g., about 0.15 inches). A portion 346 adjacent the end 342 of the choke braid 340 is then tucked or lightly crimped onto the braid 120 within the gap G between the end 332 of the choke tube 330 and the first step 302. The portion 346 of the choke braid 340 is then soldered to the braid 120, for example with a soldering iron (not shown) and by applying flux and solder to the end 342 of the choke braid 340. The portion 346 of the choke braid 340 is soldered to a portion of the braid 120 disposed within the second step 304. The soldering iron may be a flat tipped soldering iron suitable for soldering the choke braid 340 to the braid 120. During soldering of the portion 346 of the choke braid 340, care is made to prevent the solder from flowing onto the choke tube 330. During soldering of the choke braid 340 to the braid 120, the solder may fill any gaps between the braid 120 and the choke braid 340 as represented by filled gap 348 in FIG. 33.

Figure 32:
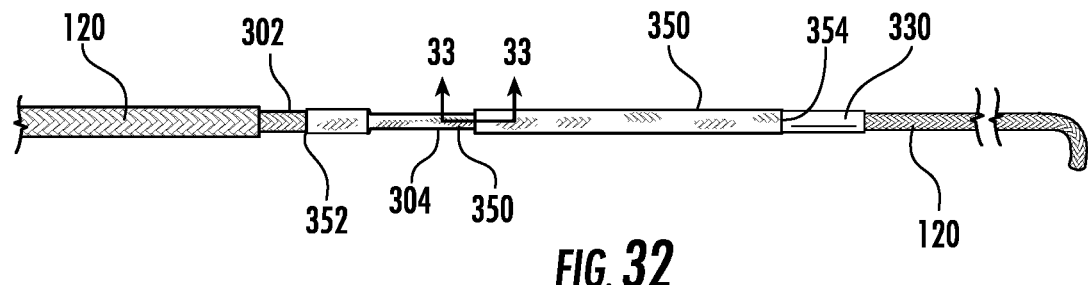
FIG. 32 is a partial side view of the radiator portion of the coaxial cable assembled to the choke braid.

Continuing to refer to FIG. 29, with the portion 346 of the choke braid 340 soldered in the gap G, the remainder of the choke braid 340 is tightened towards the end 124 of the braid 120 until the choke braid 340 is tight over the choke tube 330. Then, a third shrink tube 350 is slid over the end 124 of the braid 120, the choke braid 340, and a portion of the first step 302 such that an end 352 of the third shrink tube 350 is positioned approximately in the middle of the first step 302 (i.e., the third shrink tube 350 covers about half of the first step 302). With the end 352 of the third shrink tube 350 positioned over a portion of the first step 302 as shown in FIG. 32, the third shrink tube 350 is heated to shrink the third shrink tube 350 onto the braid 120 and the choke braid 340 to form a seal over the solder joint between the choke braid 340 and the braid 120 and to secure the choke braid 340 to the choke tube 330. The third shrink tube 350 may also prevent the solder joint between the choke braid 340 and the braid 120 from flaring. To effect shrinking of the third shrink tube 350, the third shrink tube 350, which is formed from polyethylene terephthalate (PET), is heated to a temperature suitable to begin shrinking the third shrink tube 350.

Figure 33:
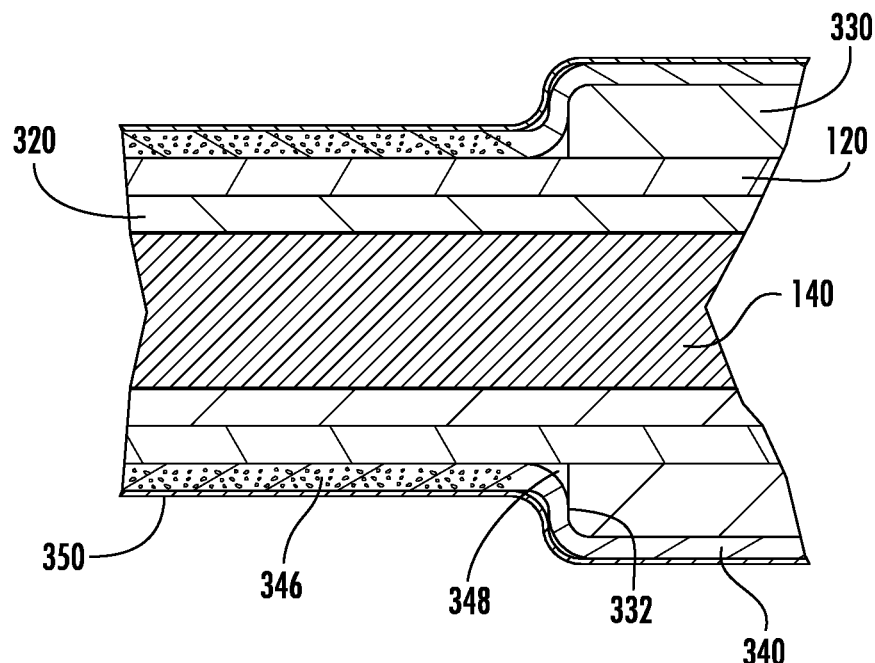
FIG. 33 is a cross-sectional view taken along section line 33-33 of FIG. 32.

With reference to FIG. 33, a joint between the choke braid 340 and the braid 120 is sealed with the third shrink tube 350. As shown, the portion 346 of the choke braid 340 is impregnated with solder and is electrically and mechanically coupled to the braid 120. The portion 346 of the choke braid 340 is covered by the third shrink tube 350.

Figure 34:
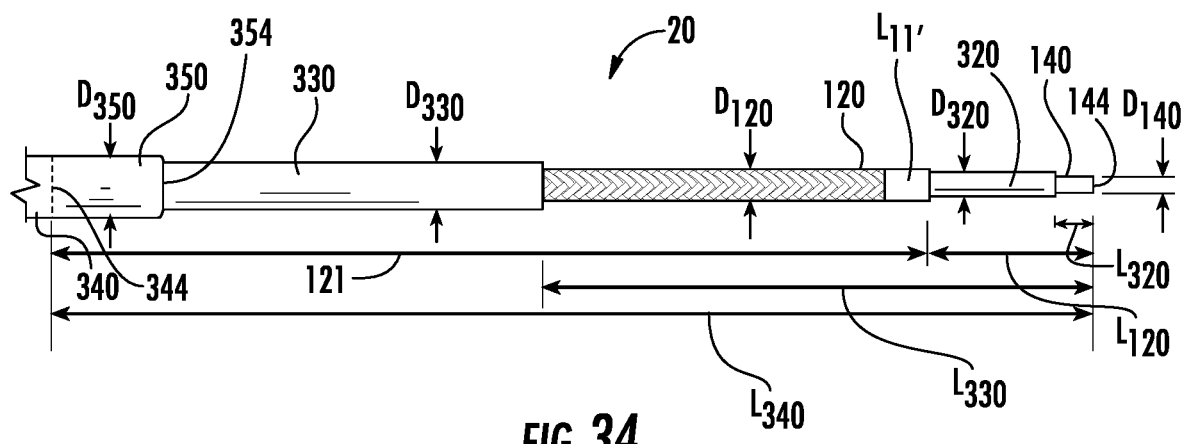
FIG. 34 is a an enlarged partial view of the radiator portion trimmed from the choke braid to a distal portion of the inner conductor.

Referring now to FIG. 34, an end 354 of the third shrink tube 350 extends over an end 344 of the choke braid 340. After the third shrink tube 350 is shrunk over the choke braid 340 and choke tube 330, the radiating portion 20 is trimmed. First the inner conductor 140 is trimmed such that the end 144 of the inner conductor 140 is a length $L_{340}$ from the end 344 of the choke braid 340. The length $L_{340}$ can be in a range of about 0.1 inches to about 2 inches (e.g., about 0.63 inches or about 16 mm). As shown, the end 354 of the third shrink tube 350 is in contact with the choke tube 330. The choke tube 330 is trimmed back a length $L_{330}$ from the end 144 of the inner conductor 140 such that a portion of the choke tube 330 is exposed between the end 344 of the choke braid 340 and the braid 120 (i.e., the outer conductor of the ablation catheter assembly 10 (FIG. 1)). The length $L_{330}$ can be in a range of about 0.1 inches to about 2 inches (e.g., about 0.5 inches or about 13 mm). The braid 120 is trimmed a length $L_{120}$ from the end 144 of the inner conductor 140 to expose a portion of the second shrink tube 320. This portion of the braid 120 forms the proximal radiating section 121. The length $L_{120}$ can be in a range of about 0.02 inches to about 2 inches (e.g., about 0.13 inches or about 3.3 mm) As shown, a portion $L_{11}$ of coated length $L_{11}$ (FIG. 27) remains over the end of the braid 120. The second shrink tube 320 is trimmed a length $L_{320}$ from the end 144 of the inner conductor 140 to expose the inner conductor 140. The length $L_{320}$ can be in a range of about 0.01 inches to about 1 inch (e.g., about 0.03 inches or about 0.7 mm). The exposed portion of second shrink tube 320 forms a feedgap 321 (FIG. 36) between the proximal radiating section 121 and a distal radiating section 360, described below. The proximal radiating section 121, feedgap 321, and distal radiating section 360 together form a dipole antenna. The choke tube 330 and choke braid 340 together form a choke or balun which is used to control the field of energy which is emitted from the dipole antenna.

The trimming of the lengths as detailed above may form the proximal radiating section 121, the feedgap 321, and the distal radiating section 360 for a particular frequency of electrosurgical energy. As will be appreciated, the lengths of the proximal radiating section 121, the feedgap 321, and the distal radiating section 360 may be proportionally adjusted to accommodate different frequencies of electrosurgical energy.

After the radiating portion 20 is trimmed, as described above, dimensions (e.g., lengths as detailed above and diameters as detailed below) of the radiating portion 20 may be verified. For example, a diameter $D_{140}$ of the inner conductor 140 may be verified to be in a range of about 0.003 inches to 0.2 inches (e.g., about 0.01 inches or about 0.2 mm), a diameter $D_{320}$ of the second shrink tube 320 may be verified to be in a range of about 0.004 inches to about 0.45 inches (e.g., about 0.01 inches or about 0.3 mm), a diameter $D_{120}$ of the braid 120 may be verified to be in a range of about 0.006 inches to about 0.5 inches (e.g., about 0.02 inches or about 0.5 mm), and a diameter $D_{330}$ of the choke tube 330 may be verified to be in a range of about 0.008 inches to about 0.49 inches (e.g., about 0.03 inches or about 0.8 mm).

Figure 35:
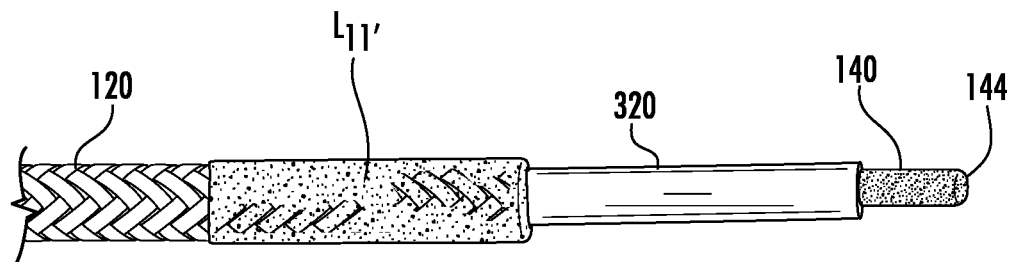
FIG. 35 is an enlarged partial view of the distal portion of the radiator portion.
Figure 36:
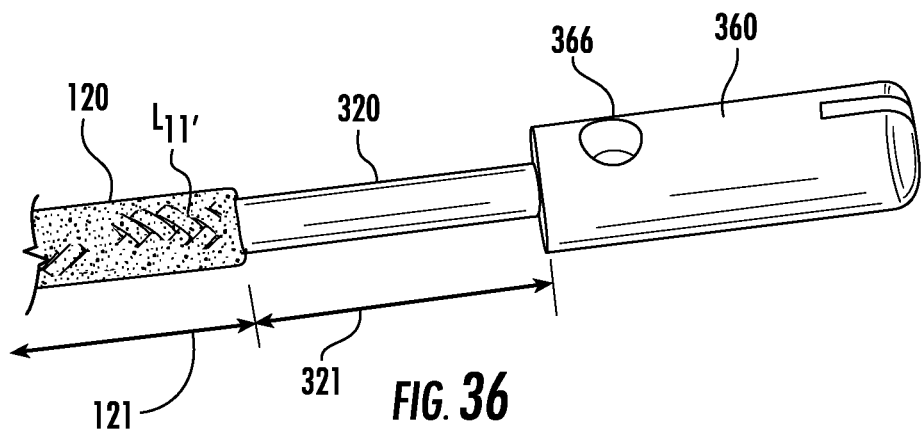
FIG. 36 is a partial perspective view of a connector disposed over the distal end of the inner connector.

With reference to FIGS. 35-36, after the radiating portion 20 is trimmed and verified, a distal radiating section 360 is attached to the end 144 of the inner conductor 140. To connect the distal radiating section 360 to the end 144 of the inner conductor 140, the distal radiating section 360 is slid over the end 144 before being soldered to the end 144. As shown, the distal radiating section 360 defines an opening 366 that permits solder to be applied to the distal radiating section 360 and the end 144 of the inner conductor 140. The distal radiating section 360 can include a champher about the opening 366 to prevent damage to the inner conductor 140. In addition, the distal radiating section 360 may include a notch that allows for increased cooling.

Figure 37:
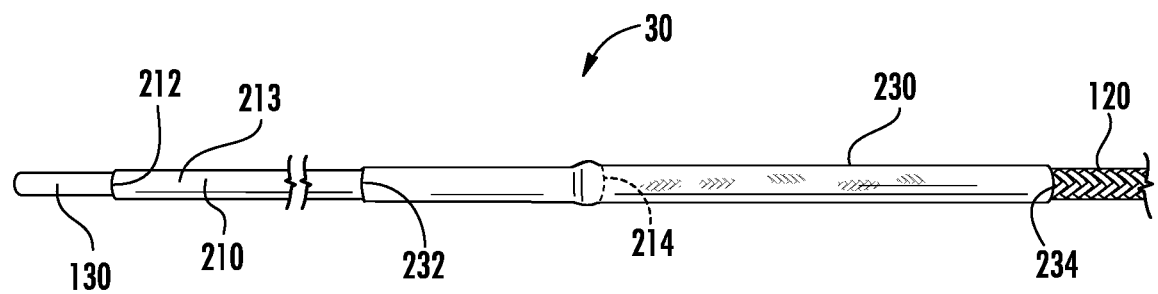
FIG. 37 is a partial side view showing the proximal connection portion with a fourth tube shrunk over the copper tube and the braid.

With reference to FIG. 37, with the radiating portion 20 completed the connection portion 30 can now be completed as described below. A fourth shrink tube 230 is disposed over the connection between the flared end portion 214 of the rigid tube 210 and the braid 120 at the connection portion 30 to prevent liquid ingress through the rigid tube 210. The fourth shrink tube 230 is slid over the end 212 of the rigid tube 210 with an end 234 of the fourth shrink tube 230 is positioned over the braid 120 about 1 inch past the end portion 214 of the rigid tube 210 with an end 232 of the fourth shrink tube 230 positioned along the rigid tube 210. With the end 234 of the fourth shrink tube 230 positioned over the braid 120, the fourth shrink tube 230 is heated to shrink the fourth shrink tube 230 onto the connection portion 30. To effect shrinking of the fourth shrink tube 230, the fourth shrink tube 230, which is formed from PET, is heated to about 400° F.

Figure 38:
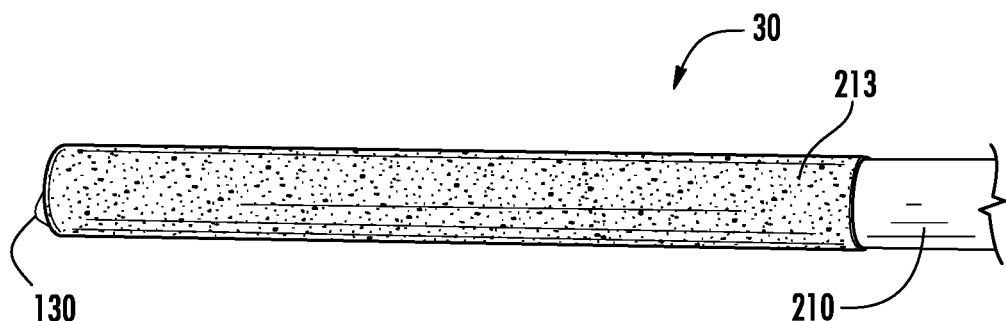
FIG. 38 is an enlarged partial view of a tin-dipped proximal portion of the copper tube of FIG. 37.

Referring to FIG. 38, after the fourth shrink tube 230 is shrunk about the rigid tube 210, the end 212 of the rigid tube 210 is cleaned. It is contemplated that about 0.5 inches of the end 212 of the rigid tube 210 is cleaned with isopropyl alcohol or similar known fluid. It will be appreciated that the wall of the rigid tube 210 is thin such that any abrasive cleaning process can weaken the rigid tube 210. After the end 212 of the rigid tube 210 is cleaned, flux is applied to a portion 213 of the rigid tube 210 adjacent the end 212 before tin dipping the portion 213 into solder for about 5 seconds. After the end 212 of the rigid tube 210 is tin-dipped, any flux residue is cleaned from the end 212. The tin dipping of the end 212 may provide wear resistance for the proximal end 212 of the rigid tube 210 as the rigid tube 210 is engaged by a source of electrosurgical energy 12 (FIG. 1).

Figure 39:
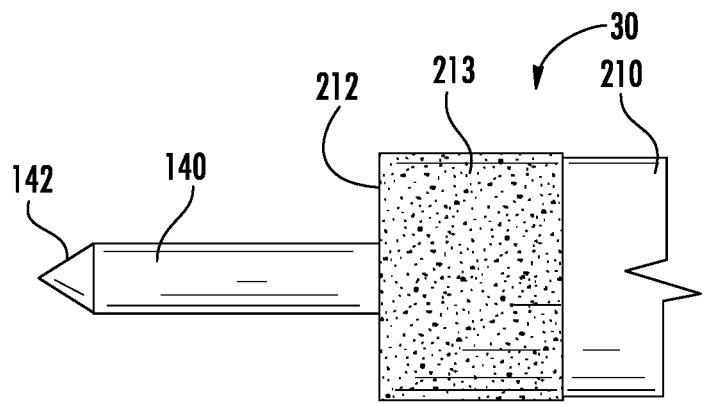
FIG. 39 is an enlarged partial view showing the proximal portion of the inner conductor extending from a proximal end of the copper tube of FIG. 38
Figure 40:
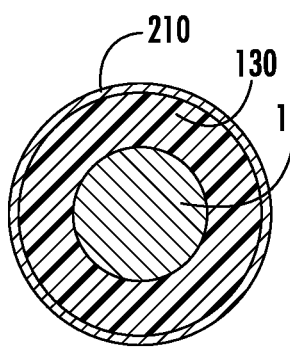
FIG. 40 is a cross-sectional view taken along section line 40-40 of FIG. 1.
Figure 41:
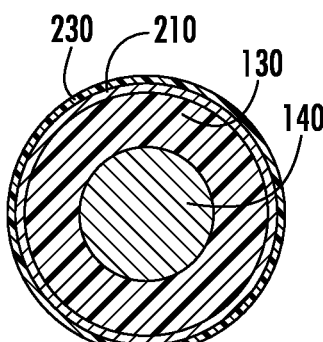
FIG. 41 is a cross-sectional view taken along section line 41-41 of FIG. 1.
Figure 42:
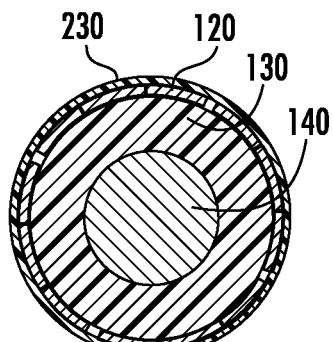
FIG. 42 is a cross-sectional view taken along section line 42-42 of FIG. 1.
Figure 43:
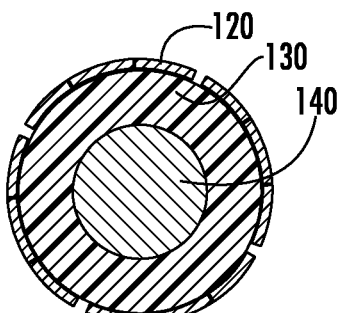
FIG. 43 is a cross-sectional view taken along section line 43-43 of FIG. 1.
Figure 44:
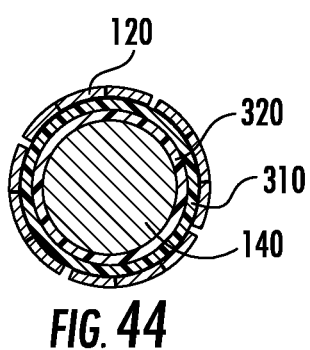
FIG. 44 is a cross-sectional view taken along section line 44-44 of FIG. 1.
Figure 45:
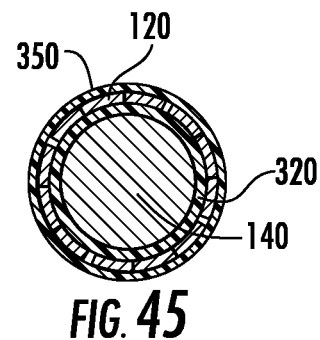
FIG. 45 is a cross-sectional view taken along section line 45-45 of FIG. 1.
Figure 46:
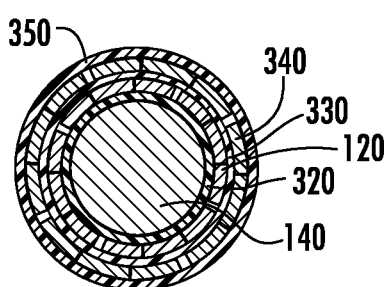
FIG. 46 is a cross-sectional view taken along section line 46-46 of FIG. 1.
Figure 47:
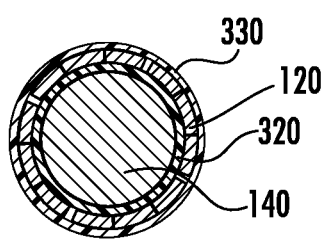
FIG. 47 is a cross-sectional view taken along section line 47-47 of FIG. 1.
Figure 48:
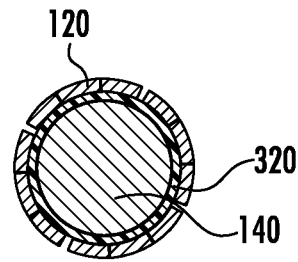
FIG. 48 is a cross-sectional view taken along section line 48-48 of FIG. 1.
Figure 49:
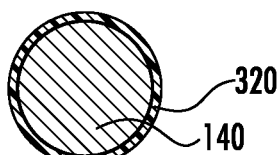
FIG. 49 is a cross-sectional view taken along section line 49-49 of FIG. 1.
Figure 50:
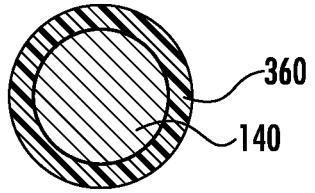
FIG. 50 is a cross-sectional view taken along section line 50-50 of FIG. 1.

With the end 212 of the rigid tube 210 tin-dipped, the tin dipped portion 213 of the rigid tube 210 and the dielectric 130 extending from the end 212 of the rigid tube 210 is stripped to expose the end 142 of the inner conductor 140 as shown in FIG. 39. A razor blade or stripping tool (not shown) may be used to strip the dielectric 130. Then the proximal end 142 of the inner conductor 140 is trimmed to extend from the proximal end 212 of the rigid tube 210 in a range of about 0.01 inches to about 3 inches or in a range of about 0.05 inches to about 0.08 inches (e.g., about 0.06 inches). After the end 142 of the inner conductor 140 is trimmed, the end 142 is sharpened or pointed as shown in FIG. 39.

After the end 142 of the inner conductor 140 is pointed, the cable assembly 10 of FIG. 1 having a liquid sealed rigid or semi-rigid connection portion 30 and a liquid pregnable flexible radiating portion 20 fully assembled from the coaxial cable 100 of FIG. 2. The outer diameter of the completed cable assembly 10 is checked to verify that the outer diameter of the completed cable assembly 10 is below a maximum diameter. If the outer diameter of the completed cable assembly 10 exceeds the maximum outer diameter the completed cable assembly 10 is discarded. The maximum outer diameter of the completed cable assembly 10 may be in a range of about 0.01 inches to about 0.5 inches, 0.02 inches to about 0.4 inches, 0.03 inches to about 0.3 inches, 0.04 inches to about 0.2 inches, 0.05 inches to about 0.1 inches (e.g., about 0.045 inches). The outer diameter of the completed cable assembly 10 is measured by passing dies (not shown) of increasing size over the completed cable assembly 10 until one of the dies passes over the length of the completed cable assembly 10. If a die does not pass over the length of the completed cable assembly 10, the next size die is selected to pass over the completed cable assembly 10. The point at which each die stops (i.e., the outer diameter of the completed cable assembly 10 is larger than the die), may be recorded with other critical values of the cable assembly 10.

Referring to FIGS. 1 and 40-50, layers of the completed cable assembly 10 are shown at different positions along the length of the completed cable assembly 10. As detailed above the completed cable assembly 10 is formed from the coaxial cable 100 (FIG. 2) (i.e., the inner conductor 140, the dielectric 130, and the braid 120), the rigid tube 210, the first shrink tube 310, the second shrink tube 320, the choke tube 330, the choke braid 340, the third shrink tube 350, and the fourth shrink tube 230.

By manufacturing the cable assembly 10 in this manner, the completed cable assembly 10 is capable of maintaining high power output, up to at least 150 W, while being immersed in hypotonic saline and while maintaining a spherical electromagnetic field at a small gauge size, e.g., in a range of about 6 gauge to about 20 gauge. This is accomplished by reducing or eliminating fluid ingress into the seams between dielectric segments to prevent fluid from contacting the inner conductor 140 before the distal radiating section 360, precisely positioning the conductors of the completed cable assembly 10 (e.g., the braid 120, the inner conductor 140, the rigid tube 210, the choke braid 350, the proximal radiating section 121, and the distal radiating section 360), precisely positioning the dielectric segments of the completed cable assembly 10 segments (e.g., the dielectric 130, the first shrink tube 310, the second shrink tube 320, the choke tube 340 and the feedgap 321), and maintaining tight outer dimensions of the completed cable assembly 10 while maintaining the flexibility of the completed cable assembly 10. Further, by permitting fluid to impregnate the braided outer conductor 120, the cable assembly 10 can be cooled more efficiently than cable assemblies 10 having covered or solid outer conductors.

As will be appreciated the completed cable assembly 10 may be enclosed within one or more catheters to permit fluid flow around the cable assembly 10. These catheters may have a columinal configuration, with one catheter nested within another and the cable assembly 10 in the center. Such configuration ensures fluid flow around the cable assembly 10 for cooling and susseptance or near field control purposes as well as other purposes known to those of skill in the art.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. An ablation cable assembly comprising:
   a rigid portion forming a proximal-most portion of the ablation cable assembly and configured to couple to a source of electrosurgical energy and prevent fluid ingress, the rigid portion including a rigid tube;
   a flexible central portion extending distally from the rigid tube, the flexible central portion including:
   an inner conductor;
   a dielectric disposed about the inner conductor, the inner conductor including an exposed distal portion extending distally of a distal end of the dielectric; and
   a conductive braid disposed about the dielectric and in electrical communication with the rigid tube;
   a radiating portion extending distally from the flexible central portion and configured to deliver electrosurgical energy to tissue, the radiating portion including a first shrink tube surrounding the exposed distal portion of the inner conductor and having a proximal end abutting a distal end of the dielectric, wherein the conductive braid surrounds the first shrink tube and is disposed within a joint between the distal end of the dielectric and the proximal end of the first shrink tube; and
   a second shrink tube in contact with the dielectric.

2. The ablation cable assembly according to claim 1, wherein the entire ablation cable assembly has a diameter of in the range of 0.01 inches to about 0.5 inches.

3. The ablation cable assembly according to claim 2, wherein the rigid tube is in intimate contact with the dielectric to prevent fluid ingress towards a proximal portion of the ablation cable assembly.

4. The ablation cable assembly according to claim 2, wherein a distal portion of the rigid tube fixes the position of a proximal end of the conductive braid relative to the dielectric.

5. The ablation cable assembly according to claim 4, wherein the distal portion of the rigid tube is flared over a proximal end of the conductive braid of the flexible central portion.

6. The ablation cable assembly according to claim 5, wherein the flexible portion includes an additional shrink tube shrunk over a connection defined between the flared distal portion of the rigid tube and the conductive braid to seal the connection.

7. The ablation cable assembly according to claim 1, wherein the conductive braid is in tension between the rigid portion and the radiating portion.

8. The ablation cable assembly according to claim 1, wherein the inner conductor forms a core of the flexible central portion, the conductive braid forms an outermost layer of the flexible central portion, and the dielectric is disposed between the inner conductor and the conductive braid.

9. The ablation cable assembly according to claim 8, wherein the dielectric is in direct contact with the inner conductor and the conductive braid along an entire length of the flexible central portion.

10. The ablation cable assembly according to claim 1, wherein the rigid portion includes a proximal portion of the inner conductor, the proximal portion of the inner conductor extending proximally from a proximal end of the rigid tube.

11. The ablation cable assembly according to claim 1, wherein the inner conductor extends through the flexible central portion and into the radiating portion.

12. The ablation cable assembly according to claim 1, wherein the rigid tube and a proximal portion of the inner conductor are configured to be directly coupled to a source of electrosurgical energy.

13. The ablation cable assembly according to claim 1, wherein the rigid portion includes a proximal portion of the dielectric disposed within the rigid tube.

14. The ablation cable assembly according to claim 13, wherein the rigid tube compresses the proximal portion of the dielectric.

15. An ablation cable assembly comprising:
    a rigid tube configured to directly couple to a source of electrosurgical energy;
    an inner conductor extending through the rigid tube and extending distally from the rigid tube to a distal portion of the ablation cable assembly, the inner conductor having a proximal portion extending proximally from a proximal end of the rigid tube and configured to directly couple to a source of electrosurgical energy;
    a dielectric disposed about the inner conductor and having a proximal portion disposed within the rigid tube and a distal portion extending distally from the rigid tube;
    a conductive braid disposed about the dielectric and having a proximal portion disposed between the rigid tube and the proximal portion of the dielectric, the conductive braid extending distally from the rigid tube;
    a first shrink tube surrounding the inner conductor and having a proximal end abutting a distal end of the dielectric, wherein the conductive braid surrounds the first shrink tube and is disposed within a joint between the distal end of the dielectric and the proximal end of the first shrink tube; and a second shrink tube in contact with the dielectric.

16. The ablation cable assembly according to claim 15, wherein the inner conductor, the dielectric, and the conductive braid extend from the rigid tube to a distal radiating portion, the conductive braid forming an outer surface of the ablation cable assembly between the rigid tube and the distal radiating portion.

17. The ablation cable assembly according to claim 15, wherein the rigid tube fixes the proximal portion of the conductive braid relative to the dielectric.

18. The ablation cable assembly according to claim 15, further comprising an additional shrink tube disposed over a connection between the rigid tube and the conductive braid and configured to prevent fluid ingress into the rigid tube.

19. The ablation cable assembly according to claim 15, wherein the rigid tube compresses the proximal portion of the dielectric.

20. An ablation cable assembly, comprising:

a rigid portion configured to couple to a source of electrosurgical energy and prevent fluid ingress, the rigid portion including a rigid tube;

a flexible central portion extending distally from the rigid tube, the flexible central portion including:

an inner conductor;

a dielectric disposed about the inner conductor; and a conductive braid disposed about the dielectric;

a radiating portion extending distally from the flexible central portion and configured to deliver electrosurgical energy to tissue, the radiating portion including a first shrink tube surrounding the inner conductor and having a proximal end abutting a distal end of the dielectric, wherein the conductive braid surrounds the first shrink tube; and a second shrink tube in contact with the dielectric.

\* \* \* \* \*